(12) United States Patent
Gho et al.

(10) Patent No.: US 10,675,244 B2
(45) Date of Patent: Jun. 9, 2020

(54) MICROVESICLES DERIVED FROM NUCLEATED, MAMMALIAN CELLS AND USE THEREOF

(71) Applicant: MDIMUNE INC., Seoul (KR)

(72) Inventors: Yong Song Gho, Pohang-si (KR); Yoon Keun Kim, Pohang-si (KR); Su Chul Jang, Gyeongsangbuk-do (KR); Oh Youn Kim, Seoul (KR); Dong-Sic Choi, Incheon (KR); Yae Jin Yoon, Busan (KR)

(73) Assignee: MDIMUNE INC., Seoul (KR)

( * ) Notice: Subject to any disclaimer, the term of this patent is extended or adjusted under 35 U.S.C. 154(b) by 0 days.

(21) Appl. No.: 15/959,521

(22) Filed: Apr. 23, 2018

(65) Prior Publication Data

US 2018/0296483 A1    Oct. 18, 2018

Related U.S. Application Data

(60) Continuation of application No. 14/058,023, filed on Oct. 18, 2013, now abandoned, which is a division of application No. 13/381,338, filed as application No. PCT/KR2010/004277 on Jul. 1, 2010, now abandoned.

(30) Foreign Application Priority Data

Jul. 1, 2009    (KR) .......................... 10-2009-0059947

(51) Int. Cl.
| | |
|---|---|
| *A61K 9/127* | (2006.01) |
| *A61K 9/50* | (2006.01) |
| *A61K 45/06* | (2006.01) |
| *A61K 35/15* | (2015.01) |
| *A61K 35/545* | (2015.01) |

(52) U.S. Cl.
CPC ............ *A61K 9/127* (2013.01); *A61K 9/1278* (2013.01); *A61K 9/5068* (2013.01); *A61K 35/15* (2013.01); *A61K 35/545* (2013.01); *A61K 45/06* (2013.01)

(58) Field of Classification Search
CPC ...... A61K 9/5068; A61K 45/06; A61K 35/15; A61K 35/545; A61K 9/1278; A61K 9/127; A61K 2300/00
See application file for complete search history.

(56) References Cited

U.S. PATENT DOCUMENTS

2004/0029240 A1* 2/2004 Acker .................. A61N 1/0412
                                                435/173.6
2005/0202078 A1* 9/2005 Schiffelers ............. A61K 9/127
                                                424/450

OTHER PUBLICATIONS

Hunter et al. Detection of microRNA Expression in Human Peripheral Blood Microvesicles. PLoS One (2008), 3(11), e3694, 11 pages. (Year: 2008).*
A. S. Shet. Characterizing blood microparticles: Technical aspects and challengesVascular Health and Risk Management (2008), 4(4), 769-774. (Year: 2008).*
Morse et al. A phase I study of dexosome immunotherapy in patients with advanced non-small cell lung cancer. Journal of Translational Medicine (2005), 3(9), 8 pages. (Year: 2005).*
Lamparski et al. Production and characterization of clinical grade exosomes derived from dendritic cells. Journal of Immunological Methods (2002), 270, 211-226. (Year: 2002).*
Estelles et al. Exosome nanovesicles displaying G proteincoupled receptors for drug discovery. International Journal of Nanomedicine (2007), 2(4), 751-760. (Year: 2007).*
Stoeck et al. A role for exosomes in the constitutive and stimulus-induced ectodomain cleavage of L1 and CD44. Biochem J. (2006), 393, 609-618. (Year: 2006).*

* cited by examiner

*Primary Examiner* — Sean C. Barron
(74) *Attorney, Agent, or Firm* — Vorys, Sater, Seymour & Pease LLP; Mih Suhn Koh

(57) ABSTRACT

The present invention relates to a microvesicle that is derived from nucleated mammalian cells, which are smaller than the nucleated cells. The microvesicles of the present invention can be used in the delivery of a therapeutic or diagnostic substance to specific tissues or cells, and more particularly, relates to microvesicles derived from monocytes, macrophages, dendritic cells, stem cells or the like, which can be used to deliver specific therapeutic or diagnostic substances for treating and/or diagnosing tissue associated with cancer, diseased blood vessels, inflammation, or the like.

5 Claims, 26 Drawing Sheets
(14 of 26 Drawing Sheet(s) Filed in Color)

Scale bar = 20μm

FIG. 18

■ microvesicle derived from ICAM-1 antisense-transformed cell
☐ microvesicle derived from ICAM-1 sense-transformed cell ──■── microvesicle derived from ICAM-1 antisense-transformed cell
──▲── microvesicle derived from ICAM-1 sense-transformed cell Scale bar = 20μm Scale bar = 100nm

MICROVESICLES DERIVED FROM NUCLEATED, MAMMALIAN CELLS AND USE THEREOF

TECHNICAL FIELD

The present invention relates to microvesicles derived from nucleated mammalian cells and the use thereof in the delivery of therapeutic and/or diagnostic substances.

BACKGROUND ART

A drug delivery system (DDS) is intended to aid the delivery of medicine to a target site within the body to bring about a therapeutic effect. For example, if a medicine is excreted too fast from the body due to its low absorption or bioavailability rates, a DDS may be used to modify the drug release profile. Medicines with serious adverse effects need to be delivered to target tissues or cells only. Many currently available anticancer agents, for example, exhibit cytotoxicity on normal cells as well as on cancerous cells. The substantial delivery of anticancer agents to cancerous cells or tissues would reduce the agony and inconvenience of cancer patients during treatment.

Since the first use thereof in the 1960s, liposomes have been widely studied for their use in DDS. Advances in liposome research have constructed, in conjugation with polymers such as polyethylene glycol (PEG) studding the outside of the membrane, so-called stealth liposomes, which can avoid detection by the body's immune system. The PEG coating allows for longer circulatory half-life for the drug delivery mechanism. In practice, DOXIL, a pegylated liposome-encapsulated form of doxorubicin, has been developed. However, liposomes and stealth liposomes themselves cannot deliver drugs to target cells or tissues because they lack the ability to recognize the target cells or tissues. To allow liposomes to bind to a specific target, studies have recently been directed toward the impartment of targeting ligands, such as monoclonal antibodies, to liposomes, but none of them have yet passed clinical tests and been successfully commercialized.

Instead of artificially synthesized liposomes consisting of lipids, naturally occurring cellular membranes are used to develop delivery systems. Vesicles derived from transformed microorganisms grown in drug-containing media are used for drug delivery [WO 2005/079854, "Compositions and methods for targeted in vitro and in vivo drug delivery to mammalian cells via bacterially derived intact minicells"]. When vesicles, usually comprised of bacterial cell membranes, are derived from Gram-negative bacteria, they have lipopolysaccharides that may cause various adverse effects including immune responses within the body. In addition, a delivery system utilizing a human red blood cell membrane is disclosed [US 2007/0243137, "Cell and sub-cell methods for imaging and therapy"]. Materials, if loaded into vesicles constructed with red blood cell membranes, can be maintained for a long period of time in the blood because red blood cells last for 120 days in the blood. The loaded materials include image contrasting agents for enhancing medical imaging, and metal particles or ions for radiotherapy. However, the red blood cell-derived vesicles cannot be used to deliver drugs to specific cells or tissues because red blood cells lack an ability to recognize specific cells or tissues. Further, red blood cells are anucleated, therefore, transformation for the expression of ligands recognizing specific cells or tissues on the surface of red blood cell is not possible.

DISCLOSURE

Technical Problem

Leading to the present invention, intensive and thorough research into DDS, conducted by the present invention, aiming to overcome the problems encountered in the prior art, resulted in the finding that microvesicles derived from nucleated, mammalian cells, which can be transformed, can be used to effectively deliver therapeutic and/or diagnostic substances to specific cells or tissues.

It is therefore an object of the present invention to provide a composition comprising microvesicles derived from nucleated, mammalian cells, a pharmaceutical composition comprising microvesicles loaded with therapeutic and/or diagnostic substances, a method for delivering the substances to specific targets using the microvesicles, a system for delivering therapeutic or diagnostic substances, comprising the microvesicles, and a kit comprising the microvesicles.

However, the technical objects to be achieved in the present invention are not limited to those stated above and other objects may be clearly understood to those skilled in the art from the following description.

Technical Solution

In accordance with an aspect thereof, the present invention provides a composition comprising sub-cell sized microvesicles derived from nucleated mammalian cells.

The nucleated mammalian cells useful in the present invention include cells capable of targeting specific cells or tissues or expressing therapeutic or diagnostic substances. Also, the nucleated mammalian cells include cells transformed to be guided to specific cells or tissues and/or to express therapeutic and/or diagnostic substances.

The microvesicles of the present invention can be constructed using a method selected from the group consisting of extrusion, sonication, cell lysis, homogenization, freeze-thawing, electroporation, mechanical degradation, and chemical substance treatment of a suspension containing nucleated mammalian cells.

In accordance with another aspect thereof, the present invention provides a pharmaceutical composition comprising sub-cell sized, nucleated mammalian cell-derived microvesicles loaded with therapeutic or diagnostic substances.

In accordance with another aspect thereof, the present invention provides a pharmaceutical composition, comprising sub-cell sized, nucleated mammalian cell-derived shedding microvesicles loaded with therapeutic or diagnostic substances.

The therapeutic and/or diagnostic substances are derived from the nucleated cells and are foreign to the cells.

The microvesicles or shedding microvesicles of the present invention may be loaded with therapeutic and/or diagnostic substances as follows.

First, microvesicles can be prepared from a cell which has already been loaded with therapeutic and/or diagnostic substances of interest. For example, when cells are cultured in a medium containing the therapeutic and/or diagnostic substances of interest, they may contain the substances therein. Alternatively, the substances may be introduced into cells by electroporation. Microvesicles which shed from or which are constructed from the cells containing the substances by sonication, extrusion or mechanical degradation are loaded with the substances.

Next, the substances may be loaded into microvesicles in the course of the construction thereof. For instance, when a cell suspension containing substances of interest is extruded through sub-cell size filters, the microvesicles thus formed are loaded with the substances.

In another alternative, microvesicles or shedding microvesicles may be loaded with substances of interest after they are constructed or formed. For example, the loading can be achieved by incubating a suspension of microvesicles or shedding microvesicles with the substances or by electroporating the substances into already prepared microvesicles or shedding microvesicles.

However, it should be appreciated to those skilled in the art that the loading of substances of interest into microvesicles or shedding microvesicles is not limited to the above-illustrated methods.

In accordance with another aspect thereof, the present invention provides a composition for the delivery of therapeutic or diagnostic substances, comprising the sub-cell sized, nucleated mammalian cell-derived microvesicles.

In accordance with another aspect thereof, the present invention provides a composition for the delivery of therapeutic or diagnostic substances, comprising sub-cell sized, nucleated mammalian cell-derived shedding microvesicles.

In accordance with another aspect thereof, the present invention provides a delivery system of therapeutic or diagnostic substances, comprising sub-cell sized, nucleated mammalian cell-derived microvesicles.

In accordance with another aspect thereof, the present invention provides a delivery system of therapeutic or diagnostic substances, comprising sub-cell sized, nucleated mammalian cell-derived shedding microvesicles.

In accordance with another aspect thereof, the present invention provides a method for preparing microvesicles loaded with therapeutic or diagnostic substances from nucleated mammalian cells, comprising: applying a process to a suspension of the nucleated mammalian cells to construct microvesicles, said process being selected from the group consisting of extrusion, sonication, cell lysis, homogenization, freezing-thawing, electroporation, mechanical degradation and chemical substance treatment; isolating the microvesicles from the suspension; and incubating a suspension of the microvesicles isolates with therapeutic or diagnostic substances.

In accordance with another aspect thereof, the present invention provides a method for preparing microvesicles loaded with therapeutic or diagnostic substances from nucleated mammalian cells, comprising: incubating a suspension of the nucleated, mammalian cells with the therapeutic or diagnostic substances to load the therapeutic or diagnostic substances to the nucleated, mammalian cells; and applying a process to the mixed suspension to construct microvesicles, said process being selected from the group consisting of extrusion, sonication, cell lysis, homogenization, freezing-thawing, electroporation, mechanical degradation and chemical substance treatment.

In accordance with another aspect thereof, the present invention provides a method for preparing microvesicles loaded with therapeutic or diagnostic substances from nucleated, mammalian cells, comprising: adding therapeutic or diagnostic substances to a suspension of the nucleated, mammalian cells to yield a mixed suspension; and applying a process to the mixed suspension to construct microvesicles, said process being selected from the group consisting of extrusion, sonication, cell lysis, homogenization, freezing-thawing, electroporation, mechanical degradation and chemical substance treatment.

In accordance with another aspect thereof, the present invention provides a method for the preparation of shedding microvesicles loaded with therapeutic or diagnostic substances, from nucleated mammalian cells, comprising: isolating shedding microvesicles from a suspension of nucleated, mammalian cells; and incubating a suspension of the shedding microvesicles isolates in the presence of therapeutic or diagnostic substances.

In accordance with another aspect thereof, the present invention provides a method for the preparation of shedding microvesicles loaded with therapeutic or diagnostic substances, from nucleated mammalian cells, comprising: culturing a suspension of nucleated mammalian cells in the presence of therapeutic or diagnostic substances to load the therapeutic or diagnostic substances to the nucleated mammalian cells; and isolating shedding microvesicles loaded with the therapeutic or diagnostic substances from the culture.

In accordance with another aspect thereof, the present invention provides a method for delivering therapeutic or diagnostic substances to specific cells or tissues, comprising the use of sub-cell sized microvesicles, derived from nucleated mammalian cells, with the therapeutic or diagnostic substances loaded thereto.

In accordance with another aspect thereof, the present invention provides a method for delivering therapeutic or diagnostic substances to specific cells or tissues, comprising the use of sub-cell sized, shedding microvesicles, derived from nucleated mammalian cells, with the therapeutic or diagnostic substances loaded thereto.

In accordance with another aspect thereof, the present invention provides a method for treating or diagnosing diseases, comprising using sub-cell sized, microvesicles, derived from nucleated mammalian cells, with therapeutic or diagnostic substances loaded thereto, to deliver the therapeutic or diagnostic substances to specific cells or tissues.

In accordance with another aspect thereof, the present invention provides a method for treating or diagnosing diseases, comprising using sub-cell sized, shedding microvesicles, derived from nucleated mammalian cells, with therapeutic or diagnostic substances loaded thereto, to deliver the therapeutic or diagnostic substances to specific cells or tissues.

In accordance with another aspect thereof, the present invention provides a kit for the diagnosis of diseases, comprising nucleated mammalian cell-derived, sub-cell sized microvesicles or shedding microvesicles loaded with primers, probes, antisense nucleic acids or antibodies as active ingredients.

Advantageous Effect

The nucleated mammalian cell-derived microvesicles or shedding microvesicles with therapeutic and/or diagnostic substances thereto in accordance with the present invention can deliver the substances to target cells or tissues selectively and effectively, whereby the possible adverse effects which might occur upon the delivery of the therapeutic substances to non-target can be eliminated, reducing the agony and inconvenience of cancer patients during treatment. In addition, the specific delivery of diagnostic substances to target cells or tissues by the microvesicles enhances therapeutic efficacy. Particularly, metastasized cancer to which conventional chemotherapy is difficult to be applied can be effectively treated with the microvesicles of the present invention, without adverse effects. In addition, the specific delivery of the diagnostic substances to target cells or tissues makes it easy to accurately diagnose cells or tissues associated with diseases.

Further, so long as it is expressed by nucleated, mammalian cells, any targeting molecules, therapeutic substances or diagnostic substances may be loaded on and/or within microvesicles or shedding microvesicles without purification. The loaded substances can perform their inherent functions effectively.

Moreover, the microvesicles or shedding microvesicles with therapeutic and/or diagnostic substances loaded thereto and the preparation method thereof in accordance with the present invention may be used for in vitro and/or in vivo treatment and/or diagnosis, or experiments.

DESCRIPTION OF DRAWINGS

The patent or application file contains at least one drawing executed in color. Copies of this patent or patent application publication with color drawing(s) will be provided by the Office upon request and payment of the necessary fee.

FIG. 18 is of photographs showing the delivery of nucleated cell-derived microvesicles to cells.

BEST MODE

Figure 1:
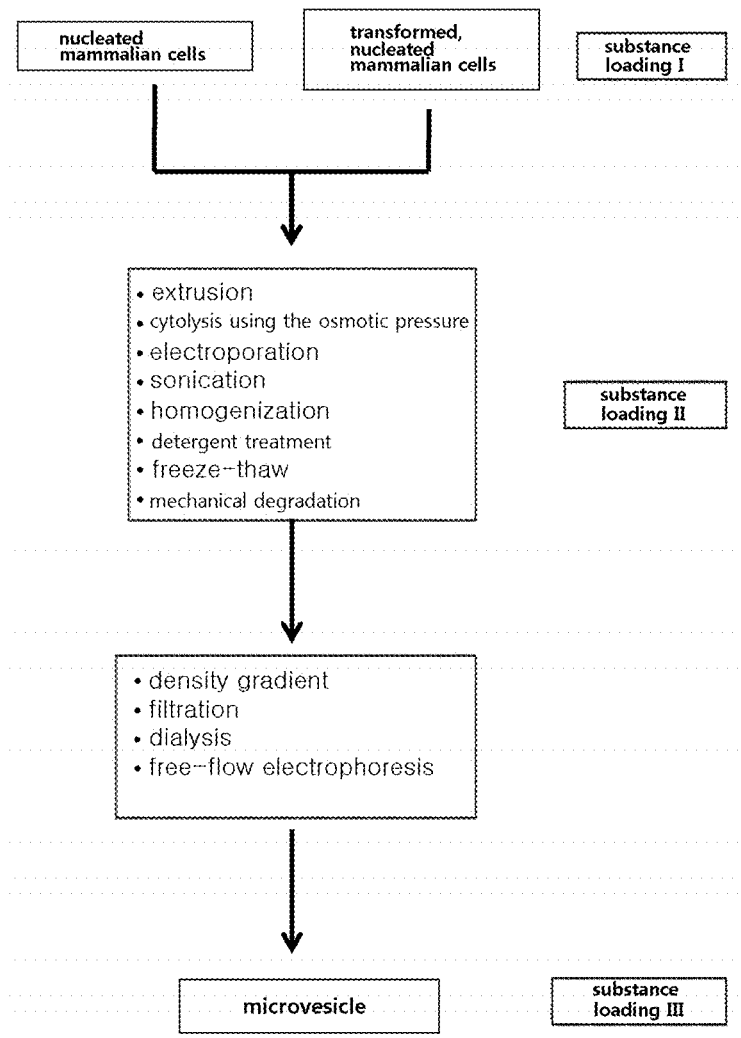
FIG. 1 is a schematic view illustrating a procedure of constructing microvesicles loaded with various substances including targeting molecules, therapeutic substances, diagnostic substances, etc.

In accordance with one aspect thereof, the present invention contemplates a composition comprising sub-cell sized microvesicles derived from nucleated mammalian cells.

Examples of the nucleated mammalian cell useful in the present invention include monocytes, macrophages, dendritic cells, and stem cells, but are not limited thereto. Further, the nucleated mammalian cells may be selected from, but are not limited to, cells differentiated from stem cells.

Distinguished from the term "shedding microvesicles" which is spontaneously secreted, the term "microvesicles," as used herein, refers to vesicles artificially synthesized from nucleated mammalian cells. A lipid bilayer derived from cell membranes forms microvesicles, defining the internal space thereof from the external environment. The microvesicles of the present invention have membrane proteins, nucleic acids and cellular components in addition to the membrane lipids, and are usually smaller than cells, but a size limit is not imposed by the present invention.

Shedding microvesicles are one that naturally sheds from cells. Likewise, a lipid bilayer derived from cell membranes forms shedding microvesicles, which have an internal space that is separated from the external environment. The shedding microvesicles are in sub-cell sized and have membrane proteins, nucleic acids and cellular components as well as membrane lipids.

The microvesicles of the present invention can be constructed using a method selected from among, but not limited to, extrusion, sonication, disruption, freeze-thawing, electroporation, mechanical degradation, and chemical substance treatment of a suspension containing nucleated, mammalian cells.

In one embodiment of the present invention, the microvesicles or shedding microvesicles further comprise components in its membrane other than those derived from the cell membrane of the nucleated mammalian cells.

The components other than those derived from the cell membrane may include targeting molecules, fusogens, which are necessary for membrane fusion with target cells, cyclodextrin, and polyethylene glycol. In addition, the components other than those derived from the cell membrane may be added using a variety of methods, including chemical modification of cell membranes.

For example, membrane components of microvesicles may be chemically modified with thiol (—SH) or amine (—$NH_2$) groups or by binding polyethylene glycol to the membrane.

A method for the preparation of microvesicles or shedding microvesicles according to the present invention may further comprise the chemical modification of membrane components.

In accordance with another aspect thereof, the present invention contemplates a pharmaceutical composition comprising sub-cell sized microvesicles with therapeutic or diagnostic substances loaded thereto, which is derived from nucleated mammalian cells.

The nucleated mammalian cells useful in the present invention may be derived into specific cells or tissues or may express therapeutic or diagnostic substances.

Further, the nucleated mammalian cells according to the present invention may include transformed cells. In detail, the transformed cells may be designed to express, but not be limited to, therapeutic substances, diagnostic substances, targeting substances, fusogens, or combination thereof.

In one embodiment of the present invention, the nucleated mammalian cells may be transformed one or more times by substance treatment or by the introduction of genetic material.

In another embodiment of the present invention, the nucleated mammalian cells may be transformed to suppress the expression of one or more specific proteins.

In another embodiment of the present invention, the nucleated mammalian cells may be transformed to express substances selected from the group consisting of cell adhesion molecules, antibodies, targeting proteins, fusogens them self and combination thereof.

In accordance with a further aspect thereof, the present invention contemplates a pharmaceutical composition comprising sub-cell sized shedding microvesicles with therapeutic or diagnostic substances loaded thereto, which is derived from nucleated mammalian cells.

No particular limitations are imparted to the substances to be loaded to the microvesicles or shedding microvesicles. For example, the substances may be one used for therapy and/or diagnosis, or proteins expressed by the nucleated mammalian cells or transformed, nucleated cells themselves. If necessary, the loading substances may be not native to the cells, but may foreign materials. That is to say, the therapeutic and/or diagnostic substances may be one derived from the nucleated cells or introduced from the outside of the cells. In addition, the loading substances may be homogeneous or heterogenous.

In another embodiment of the present invention, the microvesicles or shedding microvesicles may be prepared from cells which express or transformed to express substances selected from the group consisting of cytokines, growth factors, antibodies, targeting proteins, fusogens them self, and combination thereof, however, the cells in the present invention are not limited to the above-illustrated cells. Further, the substances may be loaded onto the surface of the microvesicles or shedding microvesicles using, but not limited to, physical, chemical and/or biological methods.

The microvesicles or shedding microvesicles of the present invention may be loaded with various foreign therapeutic and/or diagnostic substances in various manners as follows.

First, microvesicles can be prepared from cells which have already been loaded with therapeutic or diagnostic substances of interest. For example, when cells are cultured in a medium containing the therapeutic or diagnostic substances of interest, they may contain the substances therein. Alternatively, the substances may be introduced into cells by electroporation. Microvesicles which shed from or which are constructed from the cells containing the substances by sonication, extrusion or mechanical degradation are loaded with the substances.

Next, the substances may be loaded into microvesicles in the course of the construction thereof. For instance, when a cell suspension containing substances of interest is extruded through sub-cell size filters, the microvesicles thus formed are loaded with the substances.

In another alternative, microvesicles or shedding microvesicles may be loaded with substances of interest after they are constructed or formed. For example, the loading can be achieved by incubating a suspension of microvesicles or shedding microvesicles with the substances or by electroporating the substances into already prepared microvesicles or shedding microvesicles.

However, it should be appreciated to those skilled in the art that the loading of substances of interest into microvesicles or shedding microvesicles is not limited to the above-illustrated methods.

Among the therapeutic and/or diagnostic substances useful in the present invention are anticancer agents, anti-inflammatory agents, angiogenesis inhibitors, peptides, proteins, toxins, nucleic acids, beads, microparticles and nanoparticles, but the present invention is not limited thereby.

Examples of the nucleic acids include DNA, RNA, aptamers LNA (locked nucleic acid), PNA (peptide nucleic acid), and morpholinos, but are not limited thereto.

Illustrative, non-limiting examples of the nanoparticles include iron oxide, gold, carbon nanotubes, or magnetic beads.

In one embodiment of the present invention, the therapeutic and/or diagnostic substances may be fluorescent molecules, but is not limited thereto. For example, the fluorescent molecules may be fluorescent proteins or quantum dot (Q-dot).

In another embodiment of the present invention, the therapeutic and/or diagnostic substances may be anticancer agents.

The microvesicles or shedding microvesicles of the present invention may be guided to specific cells or tissues. The specific tissues may include, but are not limited to, blood vessels, cancer or inflammatory tissues.

As used herein, the term "cancer" refers to a group of different diseases, which are characterized by unregulated cell growth and infiltration to neighboring tissues due to the disruption of programmed cell death. A target to be treated according to the present invention may be selected from cancers selected from the group consisting of, but not limited to, carcinoma originating from epithelial cells, such as lung cancer, larynx cancer, stomach cancer, large intestine/rectal cancer, liver cancer, gallbladder cancer, pancreatic cancer, breast cancer, uterine cervical cancer, prostate cancer, kidney cancer, skin cancer, etc., sarcoma originating from connective tissue cells, such as bone cancer, muscle cancer, fat cancer, fiber cell cancer, etc., blood cancer originating from hematopoietic cells, such as leukemia, lymphoma, multiple myeloma, etc., and neuroma, a tumor of nervous tissues.

As used herein, the term "vascular disease" refers to a group of different diseases in which dysfunction is generated within blood vessels or in vessel walls due to metabolic, infectious, toxic or immune causes. A target to be treated according to the present invention may be selected from vascular diseases selected from the group consisting of, but not limited to, arteriosclerosis (or atherosclerosis), angina pectoris, acute myocardial infarction, stroke, vascular dementia, metabolic vascular diseases, such as ischemic vascular diseases, and infectious, toxic or immune vascular diseases such as sepsis, disseminated intravascular coagulation, thrombotic/embolism, vasculitis, nephritis, acute respiratory distress syndrome, emphysema, etc.

The term "inflammation," as used herein, refers to a syndrome or symptom including edema, resulting from an abnormal accumulation of body fluid in tissues, congestion due to vascular dilation, increased heat by pyrogen and vasodilatation, and pain induced by arachidonic acid metabolites. Inflammation may be classified as acute, subacute, and chronic inflammation according to time, and as infectious, allergic, auto-immune, toxic, metabolic and traumatic inflammatory diseases according to pathophysiological conditions. A target to be treated according to the present invention may be selected from the group consisting of, but not limited to, respiratory inflammatory diseases such as rhinitis, sinusitis, otitis media, rhinopharyngitis, laryngitis, bronchitis, asthma, chronic obstructive pulmonary disease, bronchiectasis, bronchiolitis, pneumonia, pulmonary fibrosis, etc., inflammatory diseases of the digestive system such as stomatitis, esophagitis, gastritis, peptic ulcer, irritable bowel syndrome, ulcerative colitis, cholecystitis, cholangitis, pancreatitis, hepatitis, etc., skin inflammation such as atopic dermatitis, psoriasis, etc., cardiovascular inflammatory diseases such as endocarditis, myocarditis, pericarditis, vasculitis, arteriosclerosis, sepsis, etc., inflammatory diseases of the endocrine system, such as thyroiditis, parathyroiditis, diabetes, etc., inflammatory diseases of the urogenital system such as nephritis, nephropathy, interstitial nephritis, orchitis, oophoritis, endometritis, vaginosis, etc., inflammatory diseases of the musculoskeletal system, such as rheumatoid arthritis, spondylarthritis, ostarthritis, gout, systemic lupus erythematosus, systemic sclerosis, myopathy, Sjogren syndrome, Behcet's disease, antiphospholipid syndrome, etc., inflammatory diseases of the Neuropsychiatric system, such as vascular dementia, Alzheimer's disease, degenerative brain diseases, depression, schizophrenia, and etc.

In addition to the active ingredients selected from among anticancer agents, anti-inflammatory agents, angiogenesis inhibitors, peptides, proteins, toxins, nucleic acids, beads, microparticles, nanoparticles and combinations thereof, the pharmaceutical composition of the present invention may comprise a pharmaceutically acceptable carrier, for example, saline, sterile water, Ringer's solution, buffered saline, cyclodextrin, dextrose solution, maltodextrin solution, glycerol, ethanol, liposome, or combination thereof. If necessary, the pharmaceutical composition may further comprise a typical additive such as antioxidants, buffers, etc. In addition, the pharmaceutical composition may be formulated into injections such as aqueous solutions, suspensions, emulsions, etc., pills, capsules, granules or tablets, with the aid of diluents, dispersants, surfactants, binders and/or lubricants. Moreover, the pharmaceutical composition may be formulated into suitable dosage forms according to a method well known in the art or the method disclosed in Remington's Pharmaceutical Science, Mack Publishing Company, Easton Pa. No particular limitations are imparted to the formulations of the pharmaceutical composition. Preferably, the pharmaceutical composition may be formulated into injections or inhalable forms.

No particular limitations are imparted to the administration of the pharmaceutical composition of the present invention. The pharmaceutical composition may be administered orally or parenterally such as intravenously, subcutaneously, intraperitoneally, via inhalation, or topically. The amount of the active ingredients in the pharmaceutical composition of the present invention may vary depending on various factors including patient's weight, age, gender and health condition, diet, the time of administration, the route of administration, the rate of excretion, the severity of disease, and the like. The term daily dose means an amount of the therapeutically effective ingredients of the present invention which is sufficient to reduce the condition of disease when it is administered to a subject in need thereof. A suitable dose of the active ingredients in the pharmaceutical composition of the present invention may depend on kind of the loaded compounds, disease severity, the condition of subject in need of treatment, and can be determined by those skilled in the art. For example, the suitable dose of the composition of the present invention may vary depending on patient's weight, age, gender and health condition, the route of administration, and the severity of disease, and generally ranges from 0.1 to 1000 mg/day, and preferably from 1 to 500 mg/day. The total effective amount of the pharmaceutical composition of the present invention can be administered to patients in a single dose or can be administered by a fractionated treatment protocol, in which multiple doses are administered over a more prolonged period of time.

As used herein the term "subject" refers to an animal in need of the treatment of cancer, vascular diseases or inflammatory diseases, including a human, or non-human mammals such as primates, mice, rats, dogs, cats, horses, cow, etc.

Contemplated by the present invention in accordance with still a further aspect is a composition for the delivery of therapeutic and/or diagnostic substances, comprising the microvesicles of the present invention.

The composition allows therapeutic and/or diagnostic substances to be specifically delivered to tissues or cells.

Also contemplated by the present invention in accordance with still another aspect is a composition for the delivery of therapeutic and/or diagnostic substances, comprising the microvesicles of the present invention.

In accordance with yet a further aspect thereof, the present invention contemplates a composition for the delivery of therapeutic or diagnostic substances, comprising sub-cell sized shedding microvesicles derived from nucleated mammalian cells.

In accordance with yet another aspect thereof, the present invention contemplates a delivery system of therapeutic or diagnostic substances, comprising shedding microvesicles derived from nucleated mammalian cells.

In accordance with an additional aspect thereof, the present invention contemplates a method for preparing microvesicles loaded with therapeutic or diagnostic substances from nucleated mammalian cells.

In one embodiment, the method of the present invention comprises: applying a process to a suspension of the nucleated, mammalian cells to construct microvesicles, said process being selected from the group consisting of extrusion, sonication, cell lysis, homogenization, freezing-thawing, electroporation, mechanical degradation and chemical substance treatment; isolating the microvesicles from the suspension; and incubating a suspension of the microvesicles isolates with therapeutic or diagnostic substances.

In another embodiment, the method of the present invention comprises: incubating a suspension of the nucleated, mammalian cells with the therapeutic or diagnostic substances to load the therapeutic or diagnostic substances to the nucleated, mammalian cells; and applying a process to the suspension to construct the microvesicles, said process being selected from the group consisting of extrusion, sonication, cell lysis, homogenization, freezing-thawing, electroporation, mechanical degradation and chemical substance treatment.

In another embodiment, the method of the present invention comprises: adding therapeutic or diagnostic substances to a suspension of the nucleated mammalian cells to yield a mixed suspension; and applying a process to the mixed suspension to construct microvesicles, said process being selected from the group consisting of extrusion, sonication, cell lysis, homogenization, freezing-thawing, electroporation, mechanical degradation and chemical substance treatment.

In accordance with still an additional aspect thereof, the present invention contemplates a method for the preparation of shedding microvesicles loaded with therapeutic or diagnostic substances, from nucleated mammalian cells.

In one embodiment, the method comprises: isolating shedding microvesicles from a suspension of nucleated mammalian cells; and incubating a suspension of the shedding microvesicles isolates in the presence of therapeutic or diagnostic substances.

In another embodiment, the method comprises: culturing a suspension of nucleated mammalian cells in the presence of therapeutic or diagnostic substances to load the therapeutic or diagnostic substances to the nucleated mammalian cells; and isolating shedding microvesicles loaded with the therapeutic or diagnostic substances from the culture.

The method for the preparation of microvesicles or shedding microvesicles loaded with therapeutic and/or diagnostic substances in accordance with the present invention may further comprise isolating the microvesicles or shedding microvesicles loaded with therapeutic and/or diagnostic substances from a suspension of the microvesicles or shedding microvesicles.

This isolating step may be carried out using a process selected from the group consisting of a density gradient, ultracentrifugation, filtration, dialysis and free-flow electrophoresis.

The preparation method of the present invention may further comprise adding components other than that of the cell membranes to the microvesicles membrane. The components include cyclodextrin and polyethylene glycol.

In addition, the preparation method of the present invention may further comprise chemically modifying the membrane components of the microvesicles. The chemical modification may be carried out in a manner the same as that described above.

Further, the preparation method of the present invention may further comprise removing microvesicles or shedding microvesicles whose membranes are topologically different from those of the nucleated mammalian cells.

In accordance with still another additional aspect thereof, the present invention contemplates a method for delivering therapeutic or diagnostic substances to specific cells or tissues, comprising the use of sub-cell sized microvesicles, derived from nucleated mammalian cells, with the therapeutic or diagnostic substances loaded thereto. The microvesicles of the present invention can be used to deliver therapeutic or diagnostic substances to specific cells or tissues.

In one embodiment of the present invention, two or more therapeutic or diagnostic substances may be delivered to specific cells or tissues.

For instance, two or more therapeutic or diagnostic substances may be loaded together to the same microvesicles.

In another embodiment of the present invention, microvesicles loaded with one therapeutic or diagnostic substance, microvesicles loaded with two or more therapeutic or diagnostic substances, or a combination thereof may be used to deliver the therapeutic or diagnostic substance(s). For example, two or more different microvesicles may be administered simultaneously.

In another embodiment of the present invention, two or more different microvesicles selected from the group consisting of microvesicles loaded with one therapeutic or diagnostic substance, microvesicles loaded with two or more therapeutic or diagnostic substances, and a combination thereof may be administered sequentially.

In accordance with still a further additional aspect thereof, the present invention contemplates a method for delivering therapeutic and/or diagnostic substances to specific cells or tissues, comprising the use of shedding microvesicles, derived from nucleated mammalian cells, with the therapeutic or diagnostic substances loaded thereto.

In accordance with yet still another aspect thereof, the present invention contemplates a method for treating or diagnosing diseases, comprising using sub-cell sized, microvesicles, derived from nucleated mammalian cells, with therapeutic or diagnostic substances loaded thereto, to deliver the therapeutic or diagnostic substances to specific cells or tissues.

In accordance with yet still a further aspect thereof, the present invention contemplates a method for treating or diagnosing diseases, comprising using sub-cell sized, shedding microvesicles, derived from nucleated, mammalian cells, with therapeutic or diagnostic substances loaded thereto, to deliver the therapeutic or diagnostic substances to specific cells or tissues.

In accordance with yet still an additional aspect thereof, the present invention contemplates a kit for the diagnosis of diseases, comprising nucleated mammalian cell-derived, sub-cell sized microvesicles or shedding microvesicles loaded with primers, probes, antisense nucleic acids or antibodies as active ingredients.

[Delivery of Substances Using Microvesicles or Shedding Microvesicles]

In the present invention, microvesicles or shedding microvesicles derived from cells targeting specific tissues or derived from transformed cells expressing targeting proteins may be employed. In one embodiment, the microvesicles or shedding microvesicles may be derived from transformed cells expressing fusogens.

It is known that the immune cells monocytes and their derivatives macrophages and dendritic cells, and the stem cells thereof, are guided to cancerous and inflammatory tissues. Hence, microvesicles or shedding microvesicles derived from the membrane of monocytes, macrophages, dendritic cells or the stem cells thereof are introduced into cancerous and inflammatory tissues. Further, microvesicles or shedding microvesicles derived from cells which are transformed to express proteins binding selectively to substrate expressed on specific cells or tissues can be guided to the specific cells or tissues. In the present invention, after being loaded with therapeutic or diagnostic substances, microvesicles or shedding microvesicles constructed from such cells can be used to deliver the substances to target cells, tissues or blood.

There are a variety of plasma membrane proteins that are involved in the guidance of monocytes, macrophages, dendritic cells and stem cells to specific tissues. For example, cell adhesion molecules including integrins such as LFA-1 (leukocyte function-associated antigen-1) and Mac-1 (macrophage-1 antigen) are present on the surface of monocytes. These cell adhesion molecules can bind to other cell adhesion molecules, such as ICAM-1 (intercellular adhesion molecule-1) and VCAM-1 (vascular cell adhesion molecule-1), on vascular cells. Interaction between LFA-1 and ICAM-1 allows monocytes to pass through vascular endothelial cells so that the monocytes can be directed to inflammatory or cancerous tissues.

When transformed to express plasma membrane proteins specific for cancer or tissues of interest, cells can be guided to cancer or the tissues, such as vascular tissues, cancerous or inflammatory tissues, etc. For example, ERBB2 is overexpressed on the surface of breast cancer cells. T cells can be allowed to target cancer cells by transformation to express modified T-cell receptors (TCR). T cells can be directed toward breast cancer tissue if they are transformed to express a fusion protein in which TCR is fused at its external domain to an antibody recognizing ERBB2 and at its cytoplasmic domain to CD3 $\zeta$ (zeta) responsible for intracellular signaling. Further, T cells can be guided toward large intestine cancer, pancreatic cancer and lung cancer tissue if they are transformed to express a fusion protein in which an antibody recognizing a carcinoembryonic antigen (CEA) abundantly found in the cancer tissues is fused to CD3 $\zeta$.

Cells used in the delivery of substances to target tissues or cells may be greatly influenced by the substances. For instance, because doxorubicin is too toxic, carrier cells loaded with the drug may die.

This problem may be avoided if microvesicles or shedding microvesicles derived from cells rather than cells themselves are used as the carrier. Microvesicles or shedding microvesicles derived from cells retain almost the same membrane components as those of the cells, so that they can be directed toward specific tissues or cells that the cells target. If necessary, nucleases may be employed during the construction of microvesicles or shedding microvesicles to remove nucleic acids unnecessary for the delivery of therapeutic or diagnostic substances from the microvesicles or shedding microvesicles.

[Microvesicles or Shedding Microvesicles and Preparation Thereof]

In the present invention, the term "microvesicles" means sub-cell sized vesicles, artificially synthesized from nucleated, mammalian cells, which is defined by the lipid bilayer derived from the cells and retains the same membrane proteins, nucleic acids and cytoplasmic components as those of the cells, however, the microvesicles in the present invention are not limited to the above-illustrated microvesicles. In the present invention, the term "shedding microvesicles" means sub-cell sized vesicles that are naturally sheds from nucleated, mammalian cells and thus is defined by the lipid bilayer derived from the cells and retains the same membrane proteins, nucleic acids and cytoplasmic components as those of the cells.

From cells, microvesicles can be readily constructed in various sizes like liposomes and loaded with various therapeutic or diagnostic substances to be delivered. Hence, microvesicles may be used for sole or combined therapy or diagnosis or both of therapy and diagnosis (theragnosis, pharmacodiagnosis). In this context, the substances to be delivered may be present inside the microvesicles or shedding microvesicles when encapsulated, on the surface of the microvesicles or shedding microvesicles when binding to receptors, or within the lipid bilayer when buried or embedded therein like a trans-membrane protein.

Thanks to the EPR (Enhanced Permeability and Retention) effect, generally, molecules with a size of 100 nm or larger may accumulate in cancer tissue for a longer period of time than they do in normal tissues. Accordingly, drug loaded microvesicles with a size of 100 nm or greater are advantageous in diagnosis and therapy because it can stay much longer in cancer tissue, thereby enhancing a therapeutic or diagnostic effect. On the other hand, when inhaled, only particles with a size of 1 µm or smaller are allowed to reach the alveoli due to the pulmonary structure. Substances, for example, inflammation inhibitors for the treatment of asthma, can be delivered to lung tissue if it is loaded to microvesicles which are smaller than 1 µm in size. As described, various sizes of microvesicles may be constructed depending on the tissue to which the loaded substances are to be applied. Preferably, the microvesicles of the present invention range in size from 10 nm to 10 µm.

To be administered to a subject, therapeutic and/or diagnostic substances may be loaded to the microvesicles or shedding microvesicles of the present invention. In this regard, the microvesicles or shedding microvesicles may be derived from autologous cells. Microvesicles or shedding microvesicles, if derived from heterologous cells, may provoke immune responses due to a difference in MHC (Major Histocompatibility Complex). In contrast, microvesicles or shedding microvesicles derived from autologous cells induce no immune responses. However, if MHC is compatible, heterologous cells or microvesicles or shedding microvesicles derived therefrom may be used without provoking immune responses. Further, in the case where immune responses are induced, microvesicles or shedding microvesicles may be used in combination with immunosuppressors.

In the present invention, microvesicles or shedding microvesicles may be constructed from all kinds of cells, particularly from nucleated mammalian cells that can be directed to target, such as specific cells or tissues, by transformation. For example, in vitro cells, which are cultured in vitro, such as monocytes, macrophages, dendritic cells and mesenchymal stem cells, and in vivo cells, which are taken from body tissues, such as monocytes, macrophages, dendritic cells, bone marrow- or fat-derived mesenchymal stem cells, other stem cells, cells taken from cancerous or inflammatory tissues, etc. may be sources from which the microvesicles or shedding microvesicles of the present invention can be constructed.

For use in the delivery of substances to specific tissues, microvesicles or shedding microvesicles may be constructed from intact or transformed cells which are directed toward the specific tissues. For example, microvesicles or shedding microvesicles constructed from monocytes, macrophages, dendritic cells or stem cells can target cancer or tumor tissue. Also when constructed from cells in which proteins directed toward specific tissues are upregulated and/or proteins involved in non-specific guidance are downregulated, microvesicles or shedding microvesicles can be effectively used to deliver therapeutic or diagnostic substances to tissues of interest, for example, cancer or tumor tissues.

The transformation of cells can be achieved using typical methods known in the art, for example, by stimulating the cells or introducing foreign genes into the cells to modify, e.g., upregulate or downregulate the expression of proteins of interest. A specific stimulus may induce a change in the expression of proteins of interest. For example, when treated with TNF-α, human umbilical vein endothelial cells (HUVEC) overexpress ICAM-1 in the plasma membrane [J. Exp. Med. 177; 1277-1286 (1993)]. In monocytes treated with PMA (phorbol 12-myristate 13-acetate), the membrane protein LFA-1 is activated [J. Exp. Med. 163; 1132-1149 (1986)]. The introduction of foreign genes may induce the expression or inhibition of proteins of interest. In this context, plasmid DNA, RNA or virus is introduced into cells [PNAS. 90 (18); 8392-8396 (1993)] using calcium phosphate precipitation [Current Protocols in Cell Biology 20.3.1-20.3.8 (2003)], lipofectamine mediation [PNAS. 84 (21); 7413-7417 (1987)], electroporation [Nucleic Acids Research. 15 (3) 1311-1326 (1987)], microinjection [Mol Cell Biol. 2(9); 1145-1154 (1982)], ultrasound mediation [Human Gene Therapy. 7(11); 1339-1346 (1996)] or other methods known in the art.

After cells are transformed to express proteins or antibodies capable of binding to cancer cells, tissues or vessels or inflammatory tissues, solely or as a fusion protein on the surface thereof, microvesicles or shedding microvesicles can be constructed from the cells. In addition, microvesicles or shedding microvesicles may be prepared from cells expressing therapeutic and/or diagnostic substances or cells transformed to express therapeutic and/or diagnostic substances. Of course, cells or transformed cells in which two or more therapeutic and/or diagnostic substances are expressed may be used as a source for constructing microvesicles or shedding microvesicles. To downregulate the expression of a protein of interest, miRNA, siRNA, antisense RNA, LNA, or PNA may be employed. When microvesicles or shedding microvesicles constructed from the cells are directed toward two targets, the cells may be transformed in such a way that the expression of one or more specific proteins is inhibited to reduce the guidance of the cells to one of the two targets. Hence, the specificity in the delivery of the substance for microvesicles or shedding microvesicles derived from the transformed cells is enhanced. Alternatively, cells which have undergone two or more rounds of transformation may be used. For example, primary transformants may be subjected to secondary transformation before being used as a source for constructing microvesicles or shedding microvesicles.

Microvesicles for use in the delivery of substances may be those which are naturally shed from monocytes, macrophages, dendritic cells or stem cells. These shedding microvesicles may be obtained from cells loaded with therapeutic or diagnostic substances or may be loaded with therapeutic or diagnostic substances after being isolated. Treatment with cytochalasin D, LPA (lysophosphatidic acid), thrombin, ATP (adenosine triphosphate) or KCl promotes the secretion of shedding microvesicles from cells. Cytochalasin D changes the structure of actin to promote the secretion of shedding microvesicles from cell membranes. In a flow of a cell suspension, cells and the suspension relatively move to promote the formation of shedding microvesicles. However, these methods do not limit the present invention.

The microvesicles according to the present invention may be constructed using various mechanical, electrical or chemical methods. Among the methods, cell lysis using osmosis, electroporation, sonication, homogenization, detergent treatment, freeze-thawing, extrusion, mechanical degradation, and chemical substance treatment can be used, but these methods do not limit the present invention. In a mechanical degradation method, a solution of cells is shaken together with metal, ceramic or sufficiently hard plastic balls. In the context of extrusion, cells are forced to sequentially pass through filters starting with large pores and going down to smaller pores. For example, cells are sequentially passed through three filters with respective pore sizes of 10 µm→5 µm→1 µm to form microvesicles.

[Therapeutic or Diagnostic Substance]

In the present invention, substances that cells or transformed, nucleated mammalian cells express or foreign substances that the nucleated mammalian cells do not express may be used, however, the therapeutic or diagnostic substances in the present invention are not limited to the above-illustrated therapeutic or diagnostic substances. As therapeutic or diagnostic substances which can be loaded to the microvesicles or shedding microvesicles of the present invention, various materials including proteins or peptides, nucleic acids, lipids and metabolites, all being derived from nucleated mammalian cells, may be used without limitations.

Examples of the loadable proteins or peptides useful in the present invention include, but are not limited to, growth factors, such as VEGF (vascular endothelial growth factor), EGF (epidermal growth factor), etc., cytokines such as IL-1, IFN-gamma, IL-10, etc., antibodies, receptors, and fluorescent proteins. The proteins or peptides may be expressed within cells or displayed on plasma membranes. Also, their entirety or active sites may be expressed solely or as fusion proteins. It is known that the activity of proteins or peptides displayed on plasma membranes is higher than when they are expressed within cells as a result of the higher local concentration. Proteins or peptides on plasma membranes may act as ligands to trigger signaling or as antagonists to inhibit the function of various ligands.

Examples of the nucleic acids loadable to the microvesicles or shedding microvesicles of the present invention include DNA, miRNA, siRNA, antisense RNA, and sense RNA, but are not limited thereto. These nucleic acids may be used to evoke sense effects, antisense effects, RNA interference, or inhibition of protein functions.

As the foreign therapeutic or diagnostic substances loadable to the microvesicles or shedding microvesicles, anti-cancer agents, anti-inflammatory agents, angiogenesis inhibitors, peptides, proteins, toxins, nucleic acids, beads, microparticles and nanoparticles may be used without limitations.

An antibody is a generic term of a drug used to suppress the growth and metastasis of cancer. Most anticancer agents act to block the replication, transcription and/or translation of cancer cells. No particular limitations are imparted to kinds of the anticancer agents useful in the present invention. Under the general principle in which kinds of cancer cells, absorption rates of anticancer agents (the duration of treatment, the route of administration, etc.), positions of tumor, sizes of tumor, etc. are taken into consideration, anticancer agents may be selected. Examples of the anticancer agents useful in the present invention include DNA alkylating agents, such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin, anti-cancer antibiotics, such as dactinomycin (actinomycin D), doxorubicin (adriamycin), epirubicin, idarubicin, mitoxantrone, plicamycin, mitomycin and C Bleomycin, and plant alkaloids, such as vincristine, vinblastine, paclitaxel, docetaxel, daunorubicin, taxol, oncovin, prednisone, cisplatin, herceptin, rituximab, etoposide, teniposide, topotecan and iridotecan. Also, radioactive substances known in the art may be used. However, the anticancer agents useful in the present invention are not limited to the examples.

Further, the anti-inflammatory agents loadable to the microvesicles or shedding microvesicles of the present invention is selected from the group consisting of, but not limited to, dexamethasone, indomethacin, ibuprofen, clobetasol propionate, diflorasone diacetate, halobetasol propionate, amcinonide, fluocinonide, mometasone furoate, desoximetasone, diclofenac and piroxicam.

As used herein, the term angiogenesis inhibitors refer to drugs that function to suppress the growth of new blood vessels from preexisting vessels. Most angiogenesis inhibitors have the function of suppressing the growth and metastasis of cancer, and inflammatory reactions. No particular limitations are imparted to the kinds of the angiogenesis inhibitors available as the therapeutic substances of the present invention.

The therapeutic or diagnostic substances loaded to the microvesicles or shedding microvesicles of the present invention may include proteins or peptides. For example, RNase A, growth factors, such as VEGF and EGF, cytokines, such as IL-1, IFN-gamma and IL-10, antibody therapeutics, DNase, and various proteins or peptides suppressing the growth and metastasis of cancer cells and inflammatory responses may be employed without limitations.

Also, the therapeutic or diagnostic substances loaded to the microvesicles or shedding microvesicles of the present invention may include toxins. The term toxin refers to a poisonous substance produced within living cells or organisms, which is capable of causing a disease on contact with or adsorption by body tissues. Using a toxin, cell death can be induced. No particular limitations are imparted to the kind of toxin available as the therapeutic substances of the present invention.

In the present invention, microvesicles or shedding microvesicles loaded with nucleic acids encoding fluorescent proteins or with various fluorescent molecules can be used for diagnosis. When microvesicles or shedding microvesicles designed to target specific cells or tissues are loaded with plasmid DNA carrying gene encoding fluorescent proteins and introduced into the body, the fluorescence signal emitted from the fluorescent proteins makes it possible to recognize where the target cells or tissues exist. Likewise, fluorescent quantum dots or other various fluorescent molecules may be loaded to microvesicles or shedding microvesicles and used to detect the position of specific cells and tissues within the body. That is, fluorescence generated from target cells or tissues can be used for diagnosis. In addition, fluorescence-emitting quantum dots may be applied to the treatment of diseases because they induce apoptosis.

Therapeutic or diagnostic substances other than fluorescent molecules, loadable to microvesicles or shedding microvesicles, may be exemplified by microparticles or nanoparticles. Examples include iron oxide particles, gold particles and carbon nanotubes, but are not limited thereto. Magnetic beads may be used as the therapeutic or diagnostic substances and loaded into the microvesicles or shedding microvesicles. Magnetic particles such as iron oxide may be used as an image contrasting agent for MRI. Moreover, nucleic acids or proteins conjugated with nanoparticles may be employed. Diagnostic radioactive substances are also available.

Two or more different substances can be delivered by the microvesicles or shedding microvesicles of the present invention. For example, the microvesicles or shedding microvesicles with two or more different substances simultaneously loaded thereto may be used to deliver the substances. Alternatively, microvesicles or shedding microvesicles loaded with different substances individually or in combination are employed in combination so that two or more different substances can be delivered. In order to deliver three different substances, for instance, first, second and third microvesicles may be loaded with the three different substances, respectively. On the other hand, fourth microvesicles with two different substances simultaneously loaded thereto and fifth microvesicles with another different substance loaded thereto may be used to deliver the three different substances. The first, the second and the third microvesicles may be used simultaneously or sequentially. Likewise, the fourth and the fifth microvesicles may be used simultaneously or sequentially.

There are various methods for isolating microvesicles or shedding microvesicles from other molecules or other cellular components, examples of which include a density gradient, ultracentrifugation, filtration, dialysis, and free flow electrophoresis, but these are not limited thereto.

A density gradient process, one of the most popular processes for distinguishing materials with different densities, can be applied to the isolation of the microvesicles or shedding microvesicles of the present invention because their densities are different from those of free molecules. For use in the density gradient process, a medium may be selected from among, but not limited to, Ficoll, glycerol, sucrose and OptiPrep™. Microvesicles loaded with or without therapeutic or diagnostic substances may be separated from each other when taking advantage of differences in density there between. A density gradient process may be used in combination with centrifugation or electrophoresis. Microvesicles or shedding microvesicles can also be isolated by gel filtration or ultrafiltration. Instead of filtration, dialysis may be adopted to remove small molecules. In addition, free flow electrophoresis is useful for isolating microvesicles or shedding microvesicles of the present invention.

According to purpose, microvesicles or shedding microvesicles within a certain size range may be selected before use. The selection of microvesicles or shedding microvesicles within a certain size range may be carried out before, simultaneously or after loading therapeutic or diagnostic substances thereinto.

In the present invention, microvesicles or shedding microvesicles in which a part of membrane components have been modified may be constructed. For example, when microvesicles are constructed from a mixture of fusion proteins and cells, the fusion proteins may be at least partially exposed on the microvesicles. Microvesicles may be converted into stealth-microvesicles by coating with polyethylene glycol. The addition of cyclodextrin to microvesicles may reduce the non-specific targeting of the microvesicles. Exhibiting both hydrophilicity and hydrophobicity, cyclodextrin, when attached onto the surface of microvesicles, can act to block non-specific binding between lipids. The microvesicles or shedding microvesicles may be chemically modified. For example, after microvesicles are constructed from cells whose membrane or trans-membrane proteins are at least in part exposed to the outside, various molecules may be chemically bound to the thiol group of cystein residues on the exposed region of the protein.

The microvesicles or shedding microvesicles with therapeutic and/or diagnostic substances loaded thereto and the preparation method thereof in accordance with the present invention may be applied to the delivery of the substances to target cells or tissues in vitro and/or in vivo. For instance, nucleated, mammalian cell-derived microvesicles with enzymes or therapeutic and/or diagnostic substances loaded thereto and a preparation method thereof may be used for in vitro experiments. Further, based on the data obtained through in vitro experiments, the microvesicles and the preparation method thereof can be applied in vivo so as to change diseased cells into curable ones.

With reference to FIG. 1 there is an illustration of a procedure of constructing microvesicles with therapeutic and diagnostic substances loaded thereto.

Figure 2:
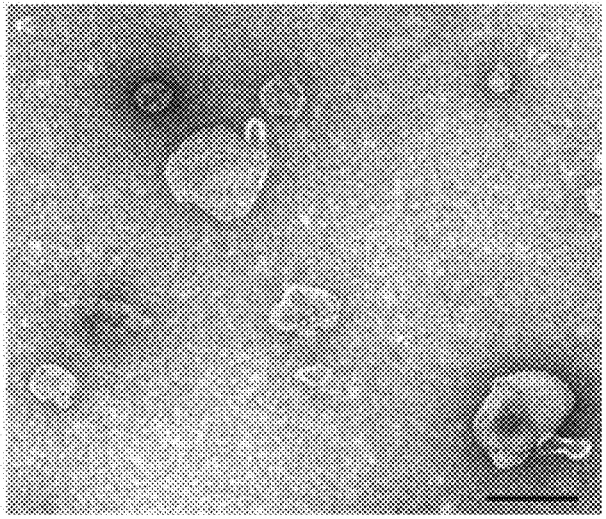
FIG. 2 is a TEM image showing microvesicles constructed from nucleated mammalian cells by extrusion.

FIG. 2 is a TEM (transmission electron microscope) image showing microvesicles constructed from monocytes by extrusion. As can be seen in the TEM image, the microvesicles are defined by lipid bilayers and are generally spherical with a size of 100~200 nm.

Figure 3:
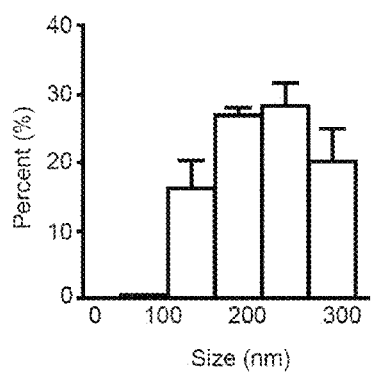
FIG. 3 is a graph showing particle sizes of microvesicles constructed from nucleated mammalian cells by extrusion.

Size distributions of the microvesicles constructed in Example 1 by extrusion are graphically shown in FIG. 3 after their sizes were measured using a dynamic light scattering (DLS) particle size analyzer. The microvesicles range in size from 200 to 300 nm with a mean size of 250 nm, which is consistent with the measurements from the TFM image of FIG. 2.

Figure 4:
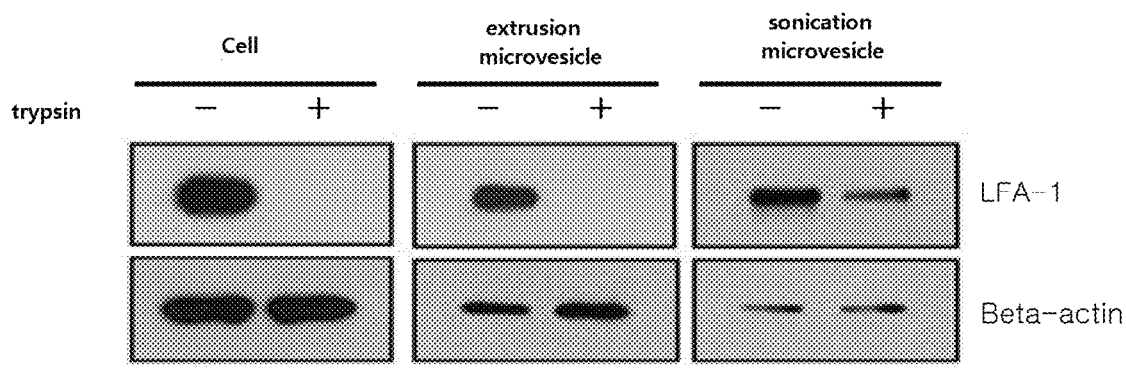
FIG. 4 is a view showing topologies of membrane proteins in monocytes, microvesicles constructed by extrusion, and microvesicles constructed by sonication.

The microvesicles constructed from monocytes in Example 1 by extrusion were found to retain the same topology as that of the plasma membrane serving as a source, as measured by the following method. Microvesicles constructed from monocytes in Example 1 by extrusion and in Example 2 by sonication were treated with trypsin to digest the externally exposed region of the membrane proteins. After the denaturation of the trypsin at a high temperature, the microvesicles were lyzed to expose all internal and membrane proteins to the solution. The solution was then treated with antibodies specific for the extracellular domain of LFA-1 or for the intracellular protein beta-actin. These immune results are shown in FIG. 4 in which '+' and '−' stand for treatment with and without trypsin, respectively. In the microvesicles constructed by extrusion after trypsin treatment, the amount of actin was reduced although the extracellular domain of LFA-1 disappeared. If even a part of the plasma membrane was turned inside out, the extracellular domain of LFA-1 might be at least in part directed toward the inside and would not be digested with trypsin, resulting in the induction of an immune response to the antibody. However, no immune responses to the LFA-1 antibody were detected, indicating that the extracellular domain of the LFA-1 of the microvesicles is directed toward the outside. From this result, it can be inferred that when microvesicles are constructed from cells by extrusion, the membrane proteins of the cells are positioned in the microvesicles in such a way that extracellular domains of the proteins are directed toward the outside of the microvesicles. Accordingly, the microvesicles have the same membrane topology as in the cells.

Referring to FIG. 4, microvesicles constructed by sonication, unlike the extruded microvesicles, showed an immune response to the LFA-1 antibody even after treatment with trypsin. Thus, when constructed by sonication, the topology of a part of the microvesicles may be the reverse of that of the source cells.

Microvesicles may be constructed using a method which may induce the topological reversal of membranes. In this regard, only those microvesicles with the same membrane topology as that of the source cells may be selected. Using antibodies recognizing cytoplasmic domains of membrane proteins, microvesicles in which the cytoplasmic domains are exposed to the outside can be removed. That is, the microvesicles in which the plasma membrane is turned inside out are removed, and only the microvesicles in which the extracellular domains of membrane proteins are positioned so as to be directed towards the outside remain.

Figure 43:
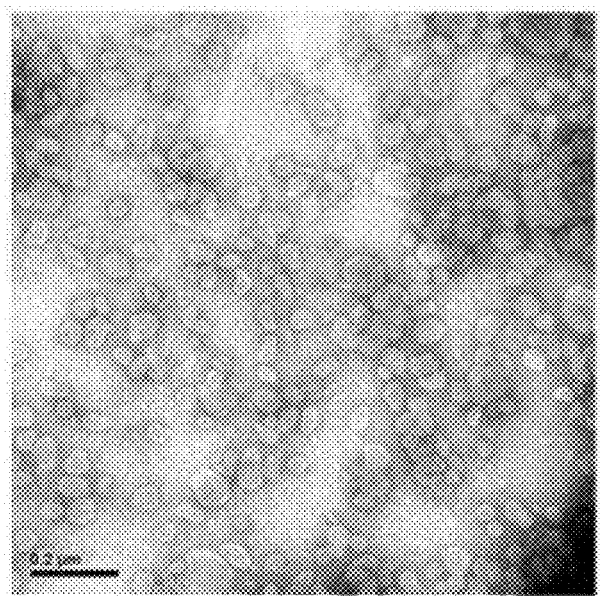
FIG. 43 is a TEM image showing shedding microvesicles derived from cytochalasin D-treated monocytes.

FIG. 43 is a TEM image showing shedding microvesicles spontaneously secreted from cells after treatment with cytochalasin D.

A better understanding of the present invention may be obtained through the following examples which are set forth to illustrate, but are not to be construed as limiting the present invention.

EXAMPLES

Example 1: Preparation of Microvesicles by Extrusion

FIG. 1 is a scheme showing a process of preparing microvesicles loaded with various substances including targeting materials, therapeutic materials and diagnostic materials from nucleated mammalian cells, whether transformed or not.

According to the procedure illustrated in the scheme of FIG. 1, microvesicles were prepared from monocytes or macrophages. From among those suggested in FIG. 1, extrusion and a density gradient were selected.

The monocyte U937 (ATCC No. CRL-1593.2) or the macrophage Raw264.7 (ATCC No. TIB-71) was resuspended at a density of $5 \times 10^6$ cells/ml in 3 mL of PBS (phosphate buffered saline). The cell suspension was passed three times through each of the membrane filters with a pore size of 10 μm, 5 μm and 1 μm, in that order. In a 5 mL untracentrifuge tube were sequentially placed 1 mL of 50% OptiPrep, 1 mL of 5% OptiPrep and 3 mL of the cell suspension effluent from the membrane filters. Ultracentrifugation at 100,000× g for 2 hours formed a layer of microvesicles between 50% OptiPrep and 5% OptiPrep.

Example 2: Preparation of Microvesicles by Sonication

According to the procedure illustrated in the scheme of FIG. 1, microvesicles were prepared from monocytes or macrophages. From among those suggested in FIG. 1, sonication and a density gradient were selected.

Monocytes or macrophages were suspended at a density of $2 \times 10^7$ cells/ml in 3 mL of PBS, followed by 30 cycles of sonication with the sonicator (UP 400 S, Hielscher) at amplitude 50%, and cycle 0.5 and then with a water bath sonicator for 30 min. In a 5 mL untracentrifuge tube were sequentially placed 1 mL of 50% OptiPrep, 1 mL of 5% OptiPrep and 3 mL of the sonicated cell suspension. Ultracentrifugation at 100,000× g for 2 hours formed a layer of microvesicles between 50% OptiPrep and 5% OptiPrep.

Example 3: Analysis of Property of Monocyte-Derived Microvesicles

The microvesicles generated from monocytes in Example 1 were adsorbed for 3 min to a glow-discharged carbon-coated copper grid. The grid was washed with distilled water and stained for 1 min with uranylacetate before observation under a JEM101 electron microscope (Jeol, Japan). The electron microscope image is shown in FIG. 2.

As can be seen in the Transmission electron microscope (TEM) image of FIG. 2, the microvesicles constructed from monocytes by extrusion consisted of a lipid bilayer and is generally spherical with a size of 100~200 nm.

The microvesicles generated from monocytes in Example 1 were diluted to a concentration of 5 μg/ml in 1 mL of PBS which was then placed in a cuvette and analyzed for particle sizes using a dynamic light scattering (DLS) particle size analyzer. The results are given in FIG. 3. As can be seen, the microvesicles ranged in size from 200 to 300 nm with a mean size of 250 nm.

With 0.5 μg of trypsin, 5 μg of each of the microvesicles generated respectively from monocytes by extrusion in Example 1 and by sonication in Example 2 was treated at 37° C. for 20 min. In the microvesicles treated with or without trypsin, 5× loading dye (250 mM Tris-HCl, 10% SDS, 0.5% bromophenol blue, 50% glycerol) was diluted finally to 1×, followed by incubation at 100° C. for 5 min. Resulting samples of microvesicles were loaded to 8% polyacrylamide gel and run at 80 V for 2 hours by electrophoresis and then transferred onto PVDF (polyvinylidene fluoride) membrane for 2 hours in the presence of an electric field of 400 mA. The membrane was blocked for 2 hours in a 3% skim milk solution in PBS before incubation with antibodies to LFA-1 and beta-actin at 4° C. for 12 hours. Then, the membrane was washed twice with PBS and incubated at room temperature for 1 hour with a peroxidase-conjugated secondary antibody. Washing with PBS for 30 min was followed by development with ECL (enhanced chemiluminescence, Amersham Co. No. RPN2106) substrate. The results are shown in FIG. 4 where '+' and '−' stand for treatment with and without trypsin, respectively.

As shown in FIG. 4, when treated with trypsin, cells and microvesicles generated by extrusion were found to lose the extracellular domain of the membrane protein LFA-1 but to retain beta-actin in the same amount as before the trypsin treatment. If even a part of the plasma membrane was turned inside out, the extracellular domain of LFA-1 was partially directed toward the inside and induced an immune response to the antibody because it was not degraded by trypsin. However, no LFA-1 antibody responses were detected in the microvesicles and cells treated with trypsin, indicating that the extracellular domain of LFA-1 present on the cells and microvesicles was directed toward the outside.

From this result, it can be inferred that when microvesicles are generated from cells by extrusion, the membrane proteins, such as LFA-1, of the cells are positioned in the microvesicles in such a way that extracellular domains of the proteins are directed toward the outside of the microvesicles. Accordingly, the microvesicles have the same membrane topology as that of the cells.

In addition, as seen in FIG. 4, microvesicles generated by sonication, unlike the extruded microvesicles, showed an immune response to the LFA-1 antibody even after treatment with trypsin. Thus, when generated by sonication, the topology of a part of the microvesicles was the reverse of that of the source cells.

Example 4: Preparation of Microvesicles Loaded with Cyclodextrin

Microvesicles were generated from monocytes in the same manner as in Example 1 and incubated with 1 μM cyclodextrin at room temperature for 1 hour. Samples were diluted to a concentration of 5 μg/ml in 1 mL of PBS which was then placed in a cuvette and analyzed for particle size using a dynamic light scattering (DLS) particle size analyzer. The results are given in FIG. 5.

Figure 5:
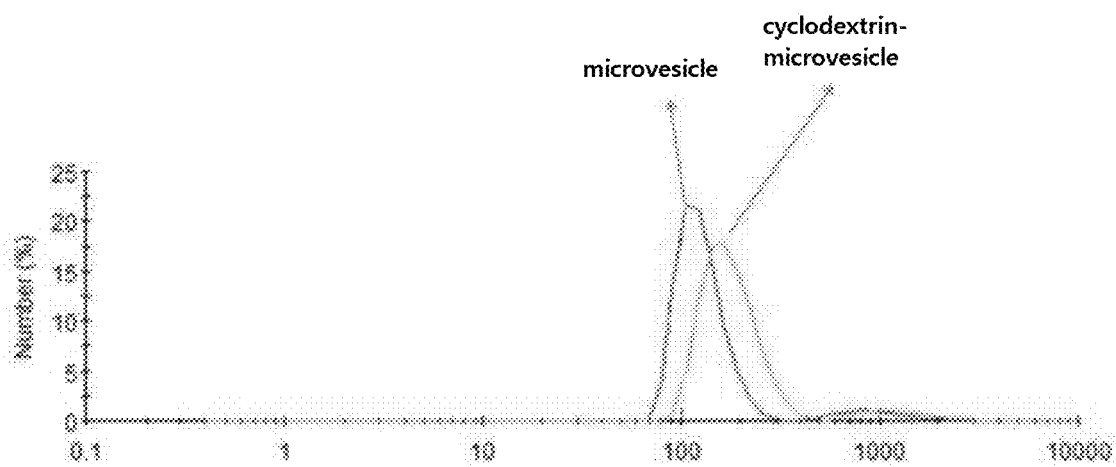
FIG. 5 is a graph showing sizes of microvesicles loaded with cyclodextrin.

As can be seen in FIG. 5, microvesicles free of cyclodextrin were about 100 nm in size, but expanded to a size of about 200 nm when loaded with cyclodextrin. From this data, it can be inferred that when incubated with cyclodextrin, the microvesicles become larger because cyclodextrin is present around the membrane.

Example 5: Preparation of Microvesicles Loaded with Polyethylene Glycol

Microvesicles were generated from monocytes in the same manner as in Example 1 and incubated with 1 μM cholesterol-polyethylene glycol at room temperature for 1 hour. Samples were diluted to a concentration of 5 μg/ml in 1 mL of PBS which was then placed in a cuvette and analyzed for particle size using a dynamic light scattering (DLS) particle size analyzer. The results are given in FIG. 6.

Figure 6:
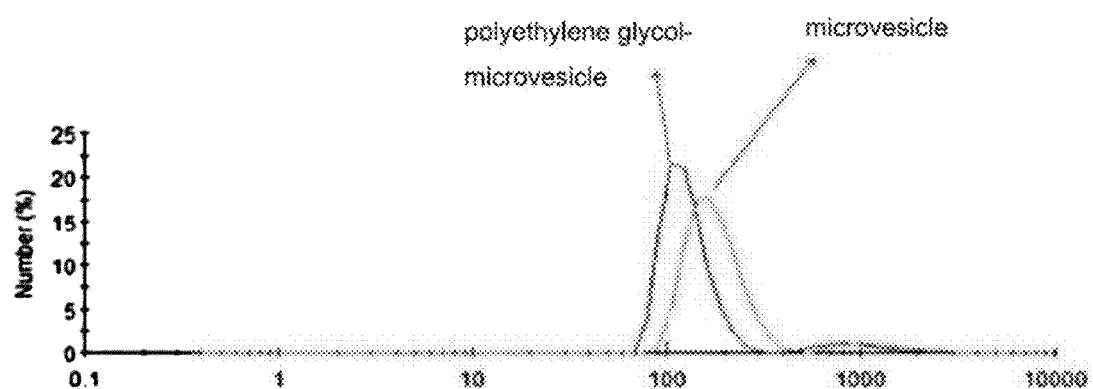
FIG. 6 is a graph showing sizes of microvesicles loaded with polyethylene glycol.

As can be seen in FIG. 6, microvesicles free of polyethylene glycol was about 100 nm in size, but shrunk to a size of about 90 nm when loaded with polyethylene glycol. From this data, it can be inferred that when incubated with polyethylene glycol, the microvesicles become smaller because polyethylene glycol is added between membrane lipid molecules.

Example 6: Preparation of Microvesicles Loaded with Cell-Derived miRNA and Intracellular Delivery of miRNA From A172 cells, a kind of human glioblastoma cell lines, expressing or not expressing the micro RNA miR125, microvesicles were generated in the same manner as in Example 1. The microvesicles derived from mrR125-expressing cells were expected to encapsulate miR125.

The presence of miR125 in the microvesicles was confirmed as follows. Based on the fact that ERBB2, a member of the EGF receptor family, acts as one of the target mRNA of miR125 [J. Biol. Chem. 282; 1479-1486 (2007)], the microvesicles were used to examine whether they interfere with EGF signaling transduction.

The human non-small cell lung cancer cell line A549 was seeded at a density of $1\times10^5$ cells/well on 6-well plates and then incubated for 12 hours. Then, the cells were treated for hour with 10 μg/ml microvesicles loaded with or without miR125 and cultured for 24 hours in a fresh culture medium. Afterwards, the cells were further cultured for an additional 12 hours in a serum-free medium, followed by treatment with 100 ng/ml EGF for 10 min. The A549 cells were lyzed in M-PER (Pierce).

Figure 7:
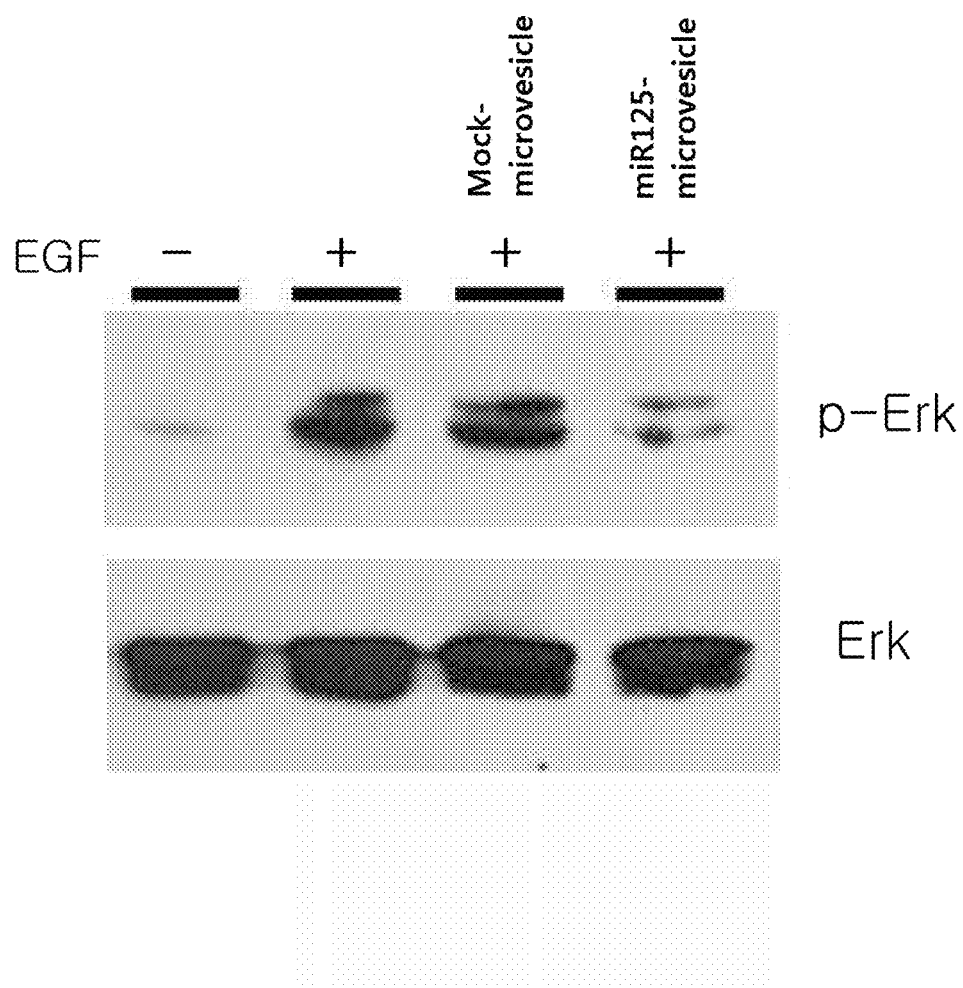
FIG. 7 is a view showing the delivery effect of miRNA after miRNA-loaded microvesicles, derived from cells, are applied to target cells.

The whole cell lysates thus obtained were separated by SDS-PAGE and subjected to Western blotting with antibodies specific for phospho-Erk (p-Erk) and Erk. FIG. 7 shows the Western blotting results. As can be seen in FIG. 7, EGF induced the expression of p-Erk whereas no p-Erk was found in the cells treated with the miR125-loaded microvesicles.

These results make it possible to infer that in the cells treated with miR125-loaded microvesicles, miR125 performs its function of reducing the expression of the EGF receptor ERBB2, resulting in the inhibition of EGF signaling.

Consequently, the data indicate that cell-derived substance can be loaded to microvesicles and delivered into cells.

Example 7: VEGF Binding Using Receptor-Loaded, Cell-Derived Microvesicles

Microvesicles were generated from human umbilical vein endothelial cells (HUVEC) in the same manner as in Example 1. Because VEGF receptors are expressed on the plasma membrane of HUVEC, the microvesicles derived from HUVEC were expected to have VEGF receptors.

Microvesicles were also generated from transformed cells expressing a VEGF receptor. In this regard, the murine cell line PT67 (ATCC No. CRL-12284) was transformed with a pCEP4 vector carrying VEGF receptor cDNA with the aid of Lipofectamine and cultured in the presence of 250 μg/ml hygromycin B (Invitrogen No. 10687010). The cells transformed to express the VEGF receptor were used to construct microvesicles in the same manner as in Example 1.

The microvesicles were plated in an amount of 0, 12.5 and 25 ng per well into well plates and incubated at 4° C. for 12 hours or longer, followed by fixation for 1 hour with 100 μl of 1% BSA/PBS. Subsequently, the microvesicles were incubated for 2 hours with 100 ng/ml biotin-conjugated VEGF and washed with 1% BSA/PBS. Incubation with streptavidin-POD for 20 min was followed by color development with a BM-POD substrate.

Figure 8:
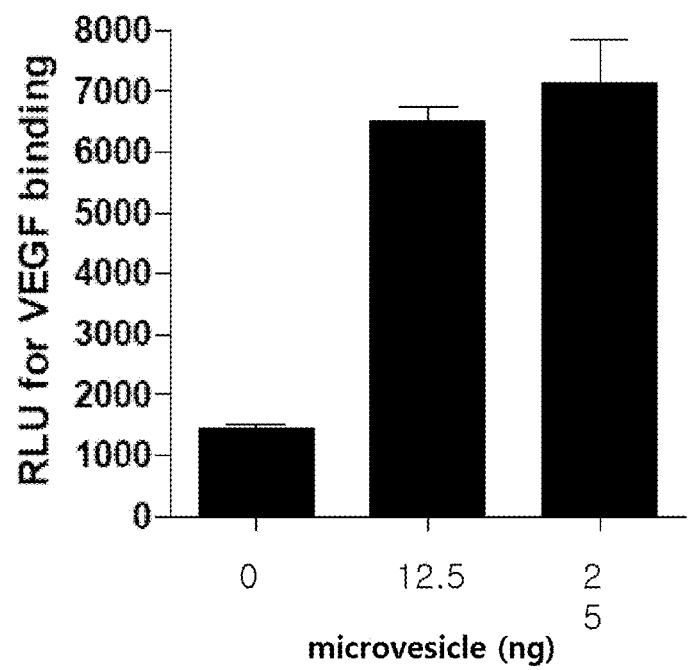
FIG. 8 is a graph showing the ability of VEGF receptor-loaded microvesicles, derived from vascular endothelial cells, to bind to VEGF.
Figure 9:
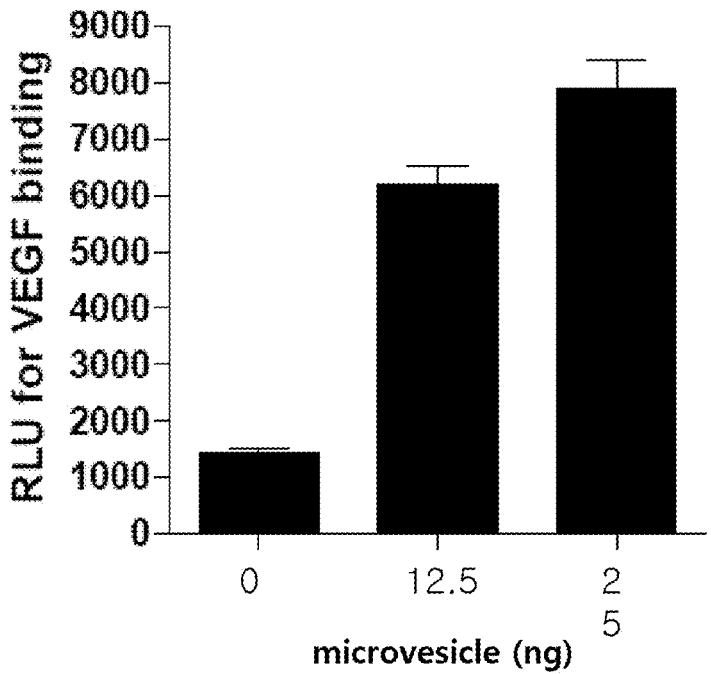
FIG. 9 is a graph showing the ability of microvesicles derived from cells transformed to express a VEGF receptor to binding to VEGF.

In FIGS. 8 and 9 are given RLU values after color development. FIGS. 8 and 9 show RLU values obtained from microvesicles derived from intact endothelial cells and cells transformed to express a VEGF receptor, respectively. RLU values represent relative numbers of VEGF bound to microvesicles. As seen in FIG. 8, the microvesicles derived from endothelial cells were found to bind to VEGF, affording high RLU values. Likewise, as seen in FIG. 9, VEGF was also found to be bound to the microvesicles derived from the cells transformed to express a VEGF receptor, showing high RLU values.

Taken together, the data demonstrate that because of being loaded onto the surface of the microvesicles, the VEGF receptor can be bound to VEGF present in the solution and that the microvesicles loaded with the VEGF receptor can be used as a VEGF antagonist.

Example 8: Inhibitory Activity of Microvesicles Derived from ICAM-1-Loaded Cells Against the Binding of Immune Cells Total RNA of the human prostate cancer cell line PC3 (ATCC No. CRL-1435) were used to generate sense ICAM-1 cDNA and antisense ICAM-1 cDNA. In this regard, a sense primer 5'-GATCGGATCCTCAGCCTCGC-TAT-GGCTCCCAGCA-3' and an antisense primer 5'-GCTAGGATCCCGGGATA-GGTTCAGGGAGGCG-3' were used for reverse transcription PCR to give the sense and antisense ICAM-1 cDNAs, respectively. The ICAM-1 cDNA, which was 1.6 kb long, was isolated on agarose gel by electrophoresis. The isolated ICAM-1 cDNA was digested with the restriction enzyme BamHI and enzymatically ligated to pCEP4 (Invitrogen No. V04450) which was also separately digested with BamHI. The resulting recombinant pCEP4 vectors respectively carrying sense and antisense ICAM-1 cDNAs transformed into the human fibroblast cell line HT1080 (ATCC No. CCL-121) with the aid of FuGENE6 transfection reagent (Roche No. 1 815 091). These cells were cultured in the presence of 250 μg/ml hygromycin B.

From the HT1080 cells in which the expression of ICAM-1 was upregulated and downregulated, respectively, by transformation with the sense and the antisense ICAM-1 cDNA, microvesicles were generated in the same manner as in Example 1.

HUVEC [J. Clin. Invest. 52; 2745-2756 (1973)] was seeded at a density of $1\times10^4$ cells/well to 96-well plates coated with 0.1% gelatin and incubated for 12 hours and then for an additional 16 hours in the presence or absence of 10 ng/ml TNF-α (Tumor Necrosis Factor-α) (R&D systems, No. 210TA). TNF-α stimulates HUVEC to increase the expression of cell adhesion molecules such as ICAM-1, VCAM-1, and E-selectin, which can bind to the cell adhesion molecules of monocytes and macrophages, such as LFA-1 and Mac-1, allowing the interaction between HUVEC, and monocytes and/or macrophages.

The monocyte U937 was loaded with 5 μM cell tracker and stained with green fluorescent dye in 30 min. After 96-well plates were washed with PBS, the green fluorescent monocytes were seeded at a density of $5 \times 10^4$ cells per well into the 96-well plates and incubated for 1 hour with the microvesicles loaded with 0, 1, 5, 25 ug/ml or free of ICAM-1. Thereafter, the culture medium was removed and the cells were washed with PBS. Green fluorescent monocytes associated with HUVEC were counted under a fluorescence microscope and the results are shown in FIG. 10.

Figure 10:
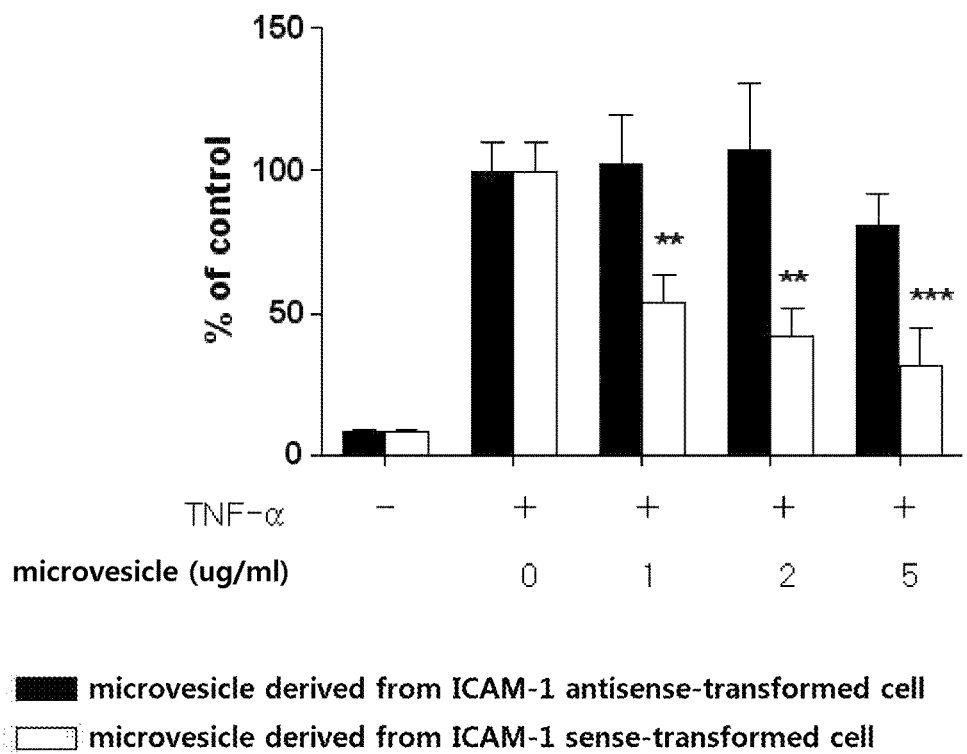
FIG. 10 is a graph showing the antagonistic effect of microvesicles, derived from cells transformed to express ICAM-1, on the interaction between immune cells and vascular endothelial cells.

In FIG. 10, the counts of green monocytes which were modified to upregulate and downregulate ICAM-1 expression by transformation with the sense and the antisense ICAM-1 are represented by white and black bars, respectively. The values of the Y-axis are expressed as percentages of the cell count of the monocytes bound to HUVEC treated with TNF-α. Stimulation with TNF-α allows HUVEC to express various cell adhesion molecules, so that HUVEC is induced to be associated with the immune cells monocytes. Almost no monocytes were detected in HUVEC which was not treated with TNF-α while monocytes were abundantly found in the HUVEC treated with TNF-α.

As can be seen in FIG. 10, the count of the monocytes bound to HUVEC increased with an increase in the concentration of ICAM-1-loaded microvesicles. However, microvesicles absent of ICAM-1 did not inhibit any binding of monocytes to HUVEC.

This data implies that ICAM-1-loaded microvesicles act as an inhibitor against the binding of monocytes to HUVEC.

Example 9: Preparation of Anticancer Agent-Loaded Microvesicles

Microvesicles were generated from monocytes or macrophages according to the scheme of FIG. 1. According to the procedure illustrated in the scheme of FIG. 1, microvesicles were prepared from monocytes or macrophages. From among those suggested in FIG. 1, extrusion and density gradient were selected. In the extrusion step, an anticancer agent was loaded to the microvesicles.

Monocytes or macrophages were suspended at a density of $5 \times 10^6$ cells/ml in 3 mL of PBS. To the cell suspension was added the anticancer drug doxorubicin (Sigma, No. D1515) at a concentration of 0, 100, 200, and 400 μg/ml. The resulting mixture was rendered to pass three times through each of the membrane filters with a pore size of 10 μm, 5 μm and 1 μm, sequentially. In a 5 mL ultracentrifugation tube were placed 1 mL of 50% OptiPrep, 1 mL of 5% OptiPrep and 3 mL of the cell suspension effluent from the membrane filters, in that order. Ultracentrifugation at 100,000× g for 2 hours formed a layer of doxorubicin-loaded microvesicles between 50% OptiPrep and 5% OptiPrep.

Doxorubicin was dissolved to a concentration of 0, 5, 10, 20, and 40 μg/ml in PBS. Microvesicles were extruded in the presence of 300 μl of each of the doxorubicin solutions. The doxorubicin-loaded microvesicles having a concentration of 100 μg/ml were plated in an amount of 100 μl in triplicate into 96-well plates. Fluorescence was quantified in the Wallac 1420 VICTOR plate reader (Perkin-Elmer Life Sciences) fitted with an excitation filter of 488 nm and an emission filter of 530 nm. A standard curve was drawn using the values from the doxorubicin solutions and used to quantify the doxorubicin incorporated into the microvesicles. The results are shown in FIG. 11.

Figure 11:
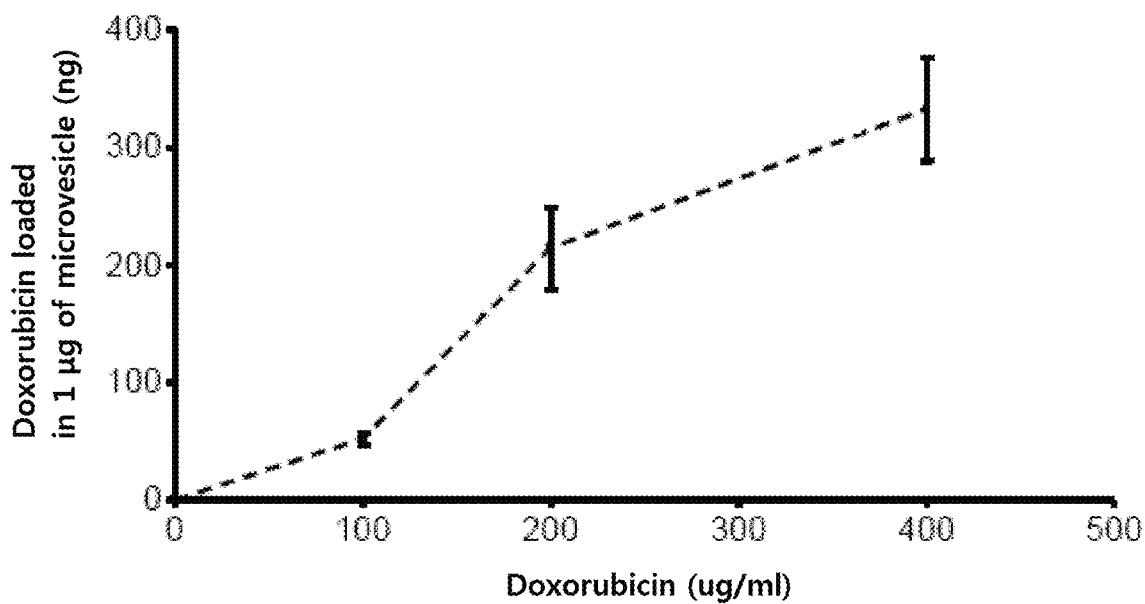
FIG. 11 is a graph showing levels of doxorubicin loaded to microvesicles various concentrations of doxorubicin used upon the construction of the microvesicles by extrusion.

FIG. 11 is a graph showing amounts of doxorubicin loaded to 1 μg of microvesicles. When doxorubicin solutions with a concentration of 100, 200, and 400 μg/ml were used, the microvesicles were observed to be loaded with doxorubicin in an amount of approximately 50 ng, 200 ng and 300 ng, respectively.

The doxorubicin-loaded microvesicles used in all of the following Examples were those generated using 400 μg/ml doxorubicin.

Example 10: Analysis of Properties of Anticancer Drug-Loaded Microvesicles

The microvesicles generated from monocytes in the same manner as in Example 1 were adsorbed for 3 min onto a glow-discharged carbon-coated copper grid which was then washed with distilled water and stained for 1 min with 2% uranylacetate. A JEM101 image of the microvesicles is given in FIG. 12.

Figure 12:
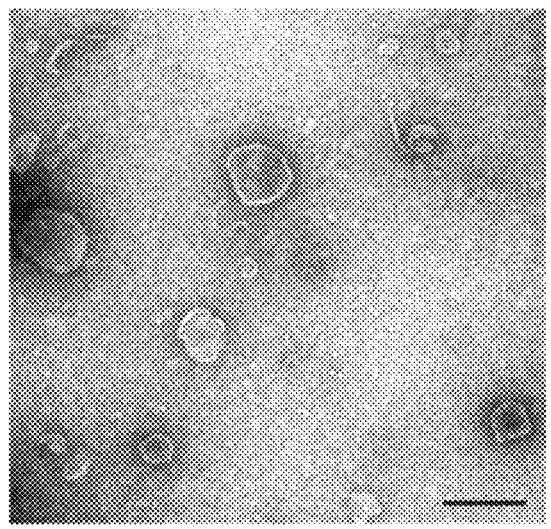
FIG. 12 is a TEM image showing doxorubicin-loaded microvesicles constructed from nucleated cells by extrusion.

As can be seen in the transmission electron microscope image of FIG. 12, the microvesicles generated from monocytes were defined by lipid bilayers and formed spheres with a size of 100~200 nm.

The microvesicles generated from monocytes in Example 9 were diluted to 5 μg/ml in 1 mL of PBS and then loaded in 1 mL cuvettes. The microvesicles were found to range in size from 100 to 300 nm with a mean size of 250 nm as measured in 1 mL cuvettes by a dynamic light scattering (DLS) particle size analyzer. The anticancer drug-loaded microvesicles were similar in size to those free of anticancer drugs.

Each of the microvesicles loaded with and without doxorubicin, respectively generated in Example 1 and 9, was incubated for 30 min with 5 μM DiO (Invitrogen, No. V22886). DiO is a liphophilic tracer with green fluorescence. DiO-labeled microvesicles were concentrated to 20 μg/ml and instilled in an amount of 50 μl on a cover glass. By incubation at 4° C. for 12 hours, the microvesicles were rendered to stick to the cover glass. This cover glass was underlayered with a slide glass. Under the fluorescence microscope, the microvesicles were observed to be fluorescent green due to DiO while doxorubicin itself appeared fluorescent red. The fluorescence images are given in FIG. 13.

Figure 13:
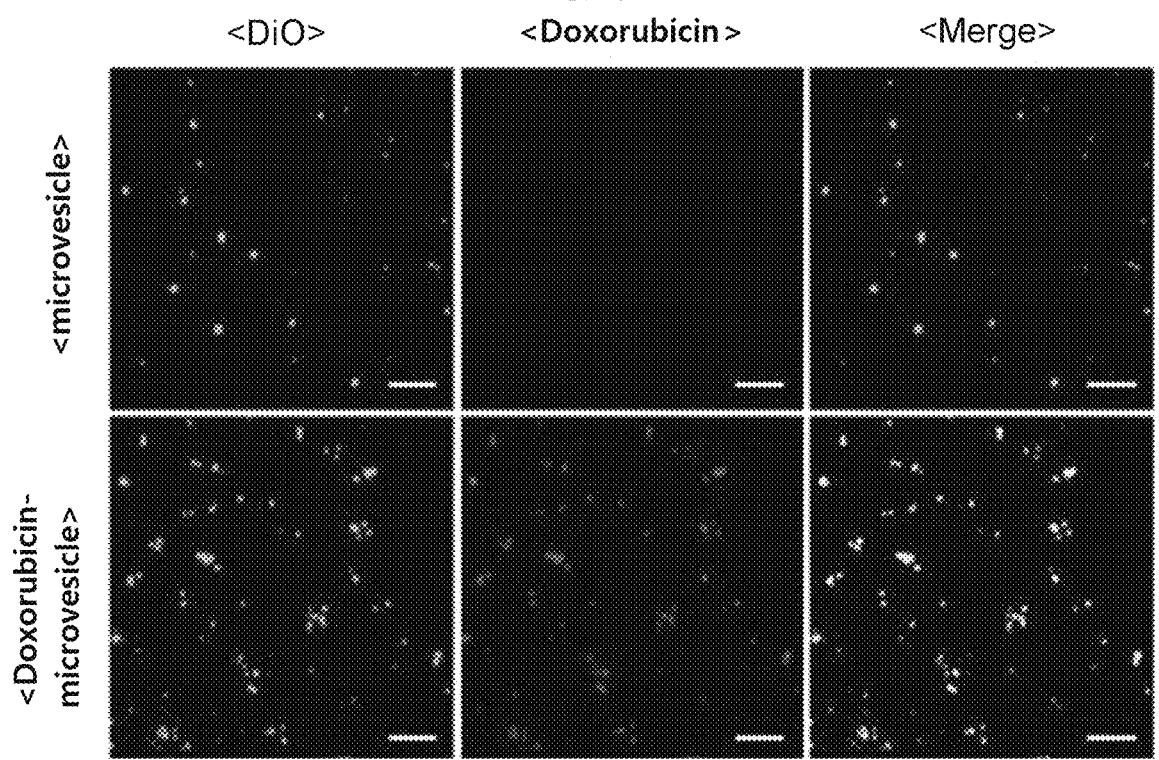
FIG. 13 is of images showing doxorubicin loaded to doxorubicin-microvesicles.

FIG. 13 shows fluorescence images of microvesicles loaded with and without doxorubicin. As shown in FIG. 13, the microvesicles, labeled with DiO, were observed as a green fluorescence with no appearance of red fluorescence of doxorubicin when they were loaded without doxorubicin. In contrast, the microvesicles loaded with doxorubicin showed the appearance of both green and red fluorescence. When the fluorescence images were merged together, the green fluorescence and the red fluorescence appeared at the same positions, confirming that doxorubicin was loaded to the microvesicles.

Example 11: Preparation of Iron Oxide-Loaded Microvesicles

Microvesicles were generated from monocytes or macrophages according to the procedure illustrated in the Scheme of FIG. 1. From among those suggested in FIG. 1, extrusion and density gradient were selected. The loading of a substance was carried out at the cellular level. Macrophages were grown to a confluence of 80% in culture plates and incubated for 24 hours with 50 µg/ml iron oxide nanoparticles. After being detached using a scrapper, the macrophages were suspended in PBS. Iron oxide-loaded microvesicles were isolated using extrusion and Optiprep as illustrated in Example 1.

Figure 14:
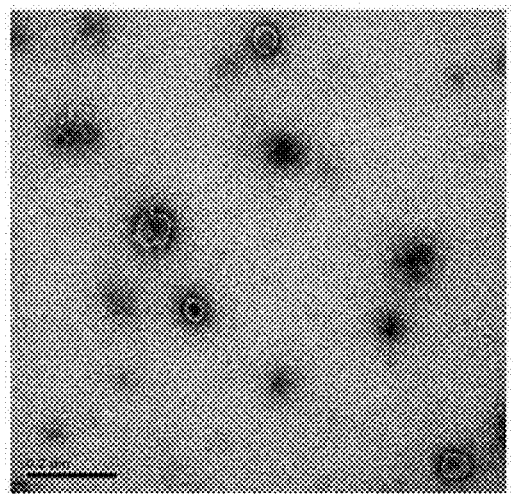
FIG. 14 is a photograph showing iron oxide-loaded microvesicles derived from nucleated cells.

FIG. 14 is a TEM image of the iron oxide-loaded microvesicles. In this image, the inside of the microvesicles appeared black as a result of the loading of black iron oxide. As shown in FIG. 14, iron oxide particles with a high electron density were encapsulated within microvesicles.

It is apparent from this result that iron oxide can be loaded into microvesicles.

Example 12: Delivery of Gene by Monocyte-Derived Microvesicles

From monocytes which were transformed by electroporation to express Green Fluorescence Protein (GFP, Clontech No. 6085-1) or Red Fluorescence Protein (RFP, Clontech No. 632465), microvesicles loaded with GFP or RFP were generated by a process similar to that of Example 9, with the exception that the loading of doxorubicin was excluded.

HT1080 cells transformed with sense ICAM-1 was seeded at a density of $1 \times 10^4$ cells/well in 24-well plates and incubated for 12 hours. After being treated for 24 hours with the 20 µg/ml GFP- or RFP-loaded microvesicles, the cells were washed with PBS and incubated 48 hours in 500 µl of a culture medium. The cells were observed under a confocal microscope. The confocal microscope images are given in FIGS. 15 and 16. DIC (Differential Interference Contrast) images were obtained using the interference of light on a confocal microscope. Hoechst dye was visualized at DAPI (4',6'-diamidino-2-phenylindole hydrochloride) wavelengths, GFP at FITC (fluorescein isothiocyanate) wavelengths, and RFP at Rhodamine wavelengths.

Figure 15:
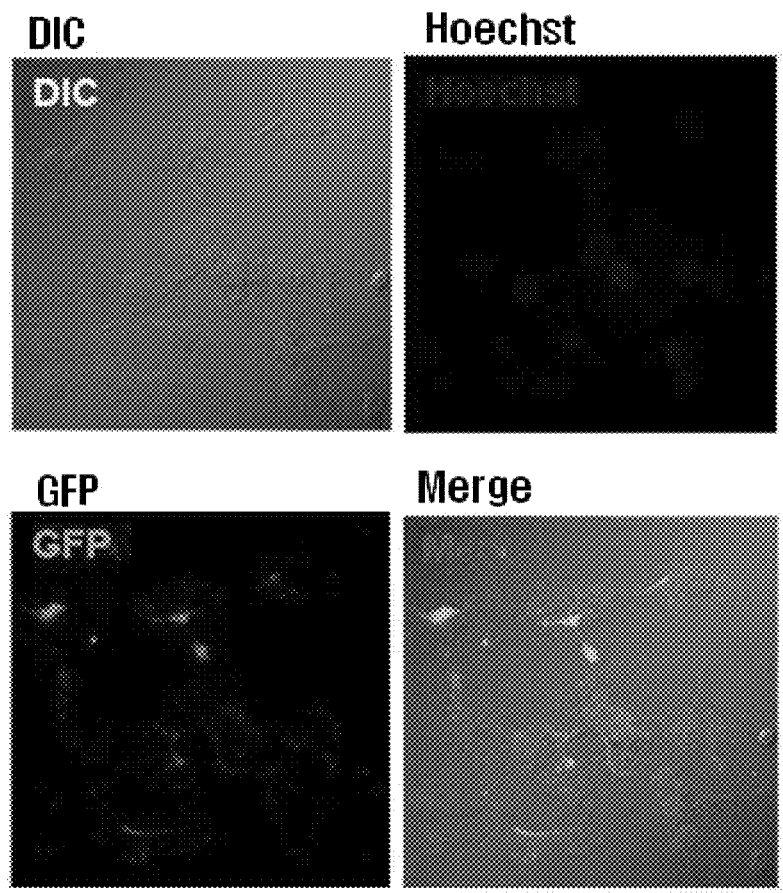
FIG. 15 is of photographs showing the delivery of a GFP gene by nucleated cell-derived microvesicles.
Figure 16:
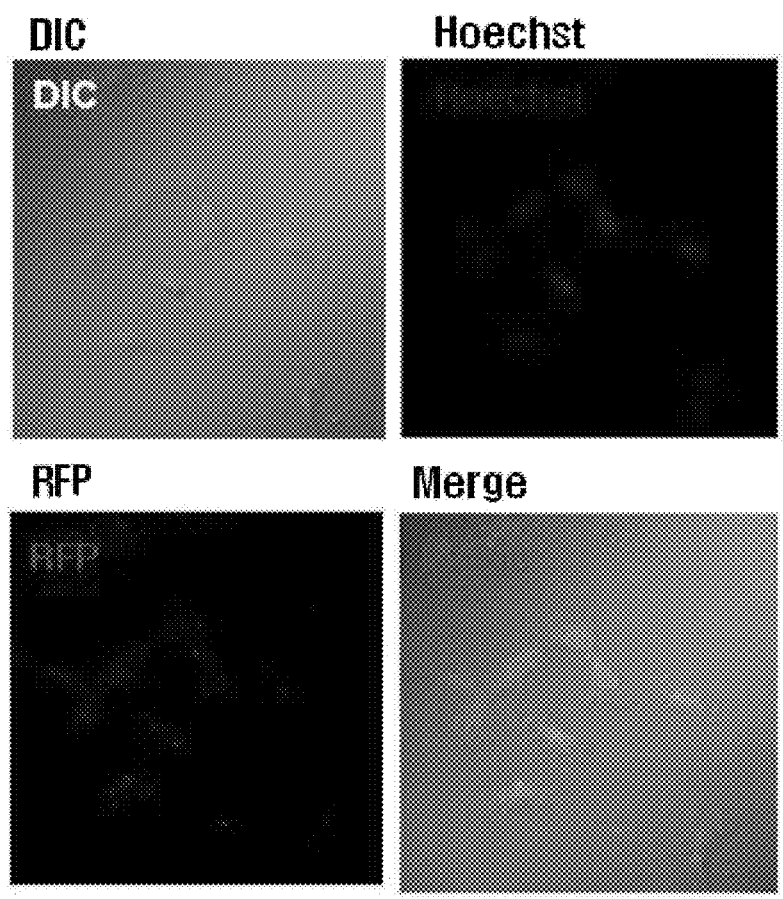
FIG. 16 is of photographs showing the delivery of an RFP gene by nucleated cell-derived microvesicles.

FIGS. 15 and 16 are images of cells to which GFP and RFP were delivered, respectively. As can be seen in FIGS. 15 and 16, the green fluorescence of GFP and the red fluorescence of RFP were detected in the cytosol.

These results demonstrate that the microvesicles can effectively deliver genes to cells.

Example 13: Delivery of Nanoparticles by Monocyte-Derived Microvesicles

Monocytes were suspended at a density of $5 \times 10^7$ cells/ml in PBS to which DiI(1,1'-dioctadecyl-3,3,3'3'-tetramethylindocarbocyanine perchlorate, Invitrogen, No. V22885) was added at a final density of 5 µM, followed by incubation at 37° C. for 30 min. After the monocytes were harvested by centrifugation at 500× g, Qdot 705 was introduced into the monocytes using electroporation. From the monocytes microvesicles were generated by a process similar to that of Example 9, with the exception that the loading of doxorubicin was excluded. Separately, microvesicles free of Qdot 705 were generated in the same manner as in Example 1.

Figure 17:
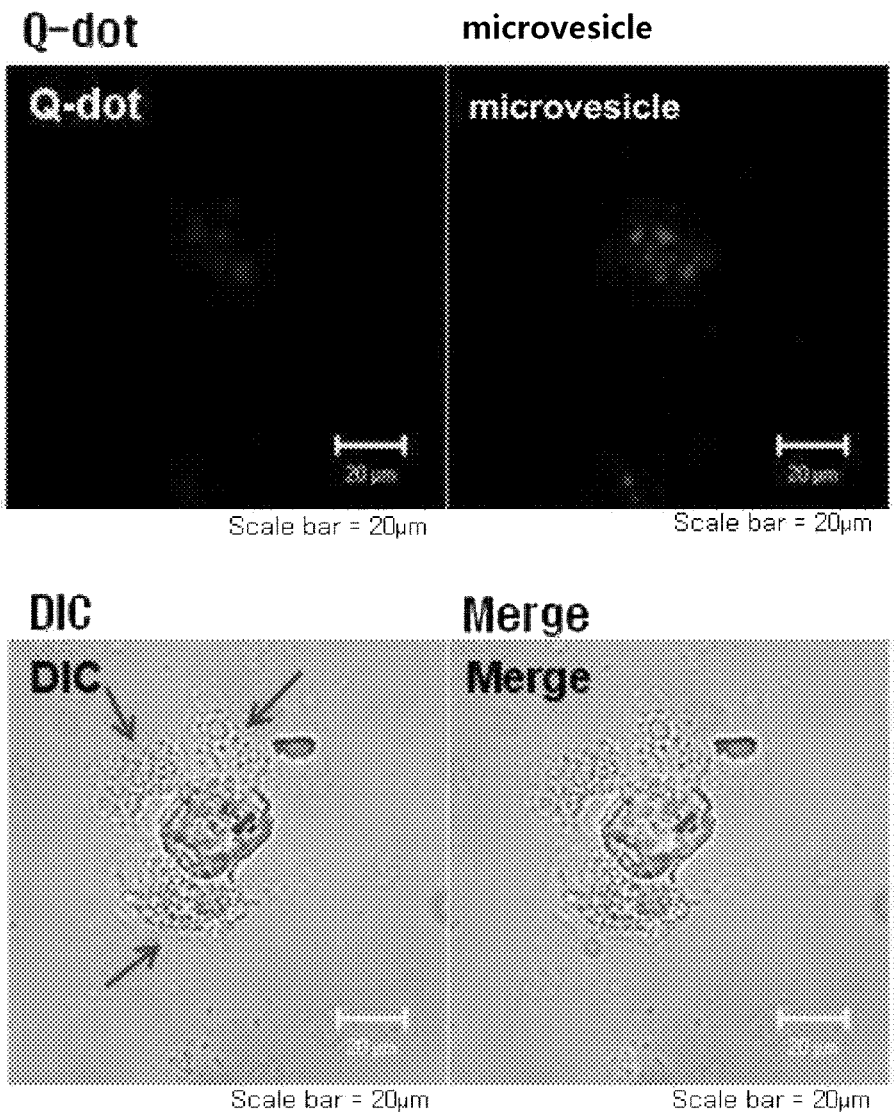
FIG. 17 is of photographs showing the delivery of the nanoparticles Q-dot by nucleated cell-derived microvesicles.
Figure 18:
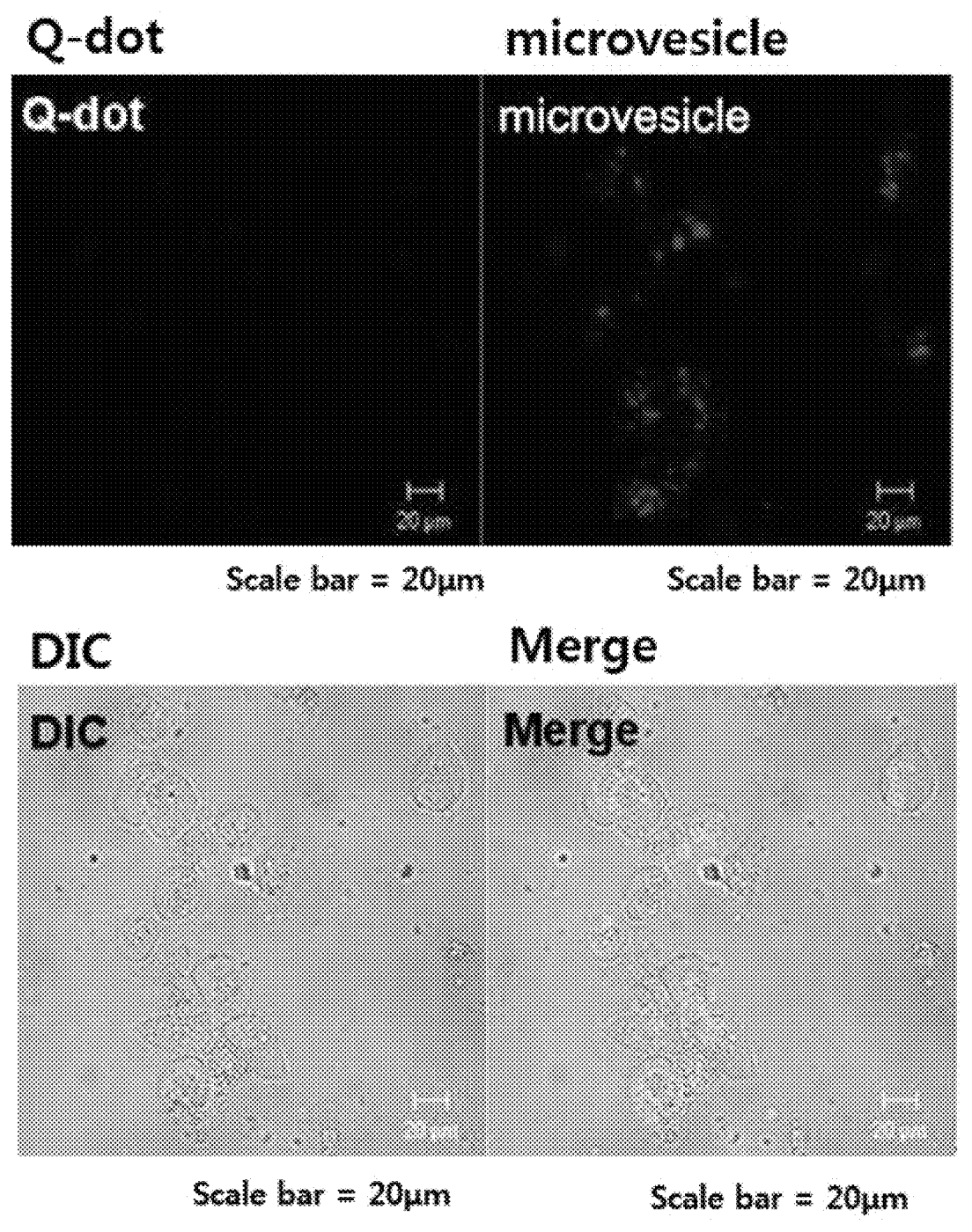

In 24-well plates was cover glass coated with 0.1% gelatin to which sense ICAM-1-transformed HT1080 were then seeded at a density of $1 \times 10^4$ cells/cover glass, followed by incubation for 12 hours. The cells were treated 24 hours with 20 µg/ml microvesicles loaded with or without Qdot 705 and then washed with PBS. The cover glass was fixed for 10 min with 4% paraformaldehyde and underlayered with a piece of slide glass. Under a confocal microscope, the cells were observed, and the images are shown in FIGS. 17 and 18. Because Qdot 705 has a wavelength gap of excitation 600 nm and emission 705 nm, fluorescence was observed at Cy7 wavelength, and represented as a pseudo color of red. Microvesicles labeled with DiI were observed to appear red fluorescent at a rhodamine wavelength. DIC images were obtained using the interference of light on a confocal microscope.

FIGS. 17 and 18 are images of cells treated with microvesicles with or without Qdot 705, respectively.

In FIG. 17, red fluorescence and blue fluorescence which are respectively derived from microvesicle and Qdot 705 are detected within the cells, demonstrating that the microvesicles and the Qdot 705 load can be effectively delivered to cells. In the DIC image of FIG. 17, cells indicated by arrows are dying and are being lyzed. When compared to the images of the microvesicles free of Qdot 705 in FIG. 18, Qdot 705 was delivered to the cells, thus inducing apoptosis.

Example 14: Delivery of Proteins by Monocyte-Derived Microvesicles

From monocytes into which RNase A (Sigma, No. R4875) was introduced by electroporation, microvesicles loaded with RNase A were generated by a process similar to that of Example 9, with the exception that the loading of doxorubicin was excluded.

HT1080 cells transformed to express sense ICAM-1 were seeded at a density of $1 \times 10^4$ cells/well into 24-well plates, incubated for 12 hours, and then treated at 37° C. for 30 min with 0, 20 or 50 µg/ml RNase-loaded microvesicles. After being washed with PBS, the cells were cultured for 24 hours in 10% FBS/MEM. The cells were washed with PBS again and incubated for 30 min with 1 µM calcein AM dye (Invitrogen, No. C3099) and 2 µM ethidium homodimer-1 dye (Invitrogen, No. E1169). Calcein AM is converted into green fluorescent calcein by the intracellular enzyme esterase. Being unable to permeate viable cells across the plasma membrane, green fluorescent calcein accumulated within viable cells. In contrast, dead cells allow calcein to readily pass through the plasma membrane thereof so that they cannot be monitored by the fluorescent signal of calcein. Ethidium homodimer-1, which emits red fluorescence when bound to nucleic acids, cannot penetrate into live cells across the plasma membrane, but can readily pass into dead cells. Accordingly, viable cells cannot be stained with ethidium homodimer-1 whereas dead cells can. That is, the fluorescence color of these two dyes are different and can be used to readily distinguish dead from viable cells. In such a manner, living and dead cells were observed under a fluorescence microscope and the results are given in FIG. 19.

Figure 19:
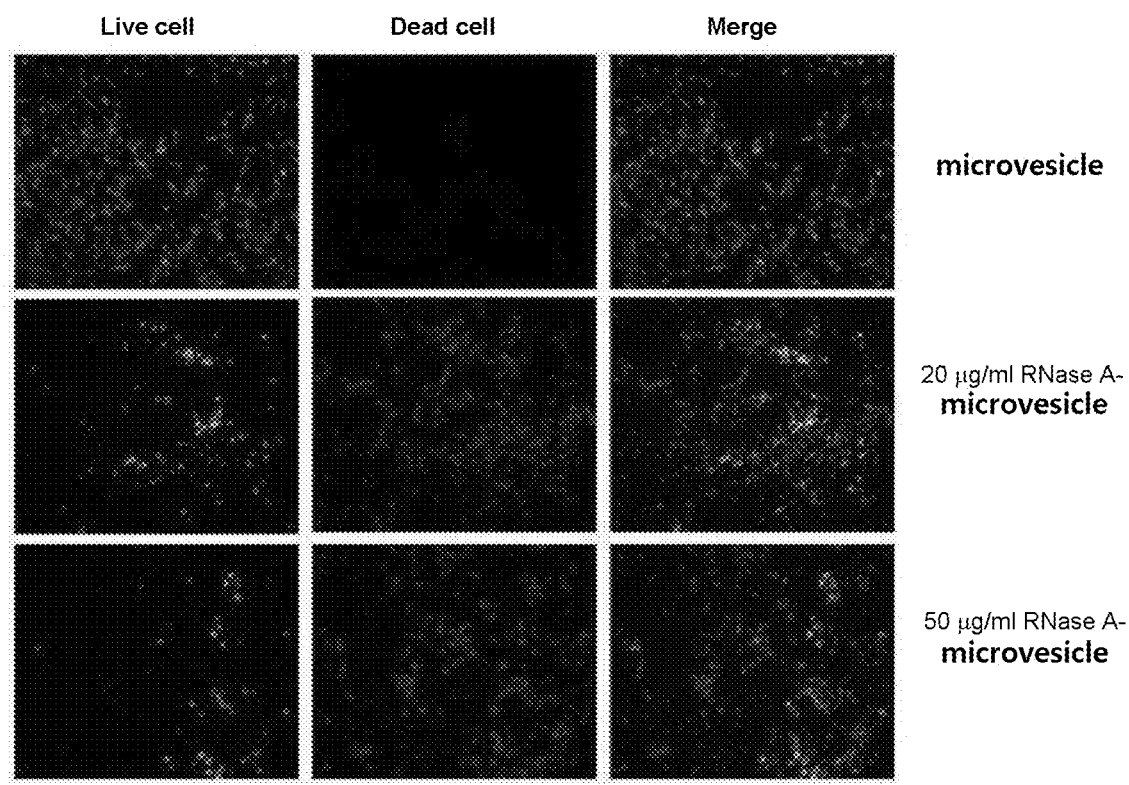
FIG. 19 is of photographs showing the delivery of RNase A to cells by nucleated cell-derived microvesicles.

As can be seen in FIG. 19, RNase A-loaded microvesicles, when applied to live cells, induced cell death in a dose-dependent manner. This result indicates that RNase A can be delivered to cells by the microvesicles of the present invention.

Example 15: Delivery of Anti-Inflammatory Drug and Inhibition of Inflammatory Reactions by Macrophage-Derived Microvesicles Macrophages were suspended at a density of $5 \times 10^6$ cells/ml in PBS, and microvesicles were generated from the cell suspension in the same manner as in Example 9, with the exception that a 400 µg/ml dexamethasone (Sigma, No. D2915) solution was used instead of doxorubicin.

To examine the anti-inflammatory effect thereof, the dexamethasone-loaded microvesicles thus obtained were applied to macrophages, which induce an immune response, after which the pro-inflammatory cytokines TNF-α and IL-6 secreted by macrophages were quantitatively analyzed using ELISA.

Macrophages were induced to evoke an inflammatory reaction by treatment with 10 ng/ml LPS (lipopolysaccharide) for 6 hours. Test groups were treated with LPS and 10 μg/ml microvesicles, simultaneously, while a control was treated with LPS alone. After treatment for 6 hours, the conditioned media were obtained and centrifuged at 500× g for 5 min. A 1% BSA/PBS solution was added in an amount of 100 μl to each well of 96-well plates coated with antibodies to TNF-α and IL-6 to block the antibodies. The conditioned media were diluted 1/10 or 1/2 and the dilutions were plated into the plates and incubated at room temperature for 2 hours. After incubation with respective biotin-conjugated, capturing antibodies to TNF-α and IL-6 for 2 hours, the cells were washed with 1% BSA/PBS. Treatment with streptavidin-POD for 20 min was followed by color development with a BM-POD substrate.

Figure 20:
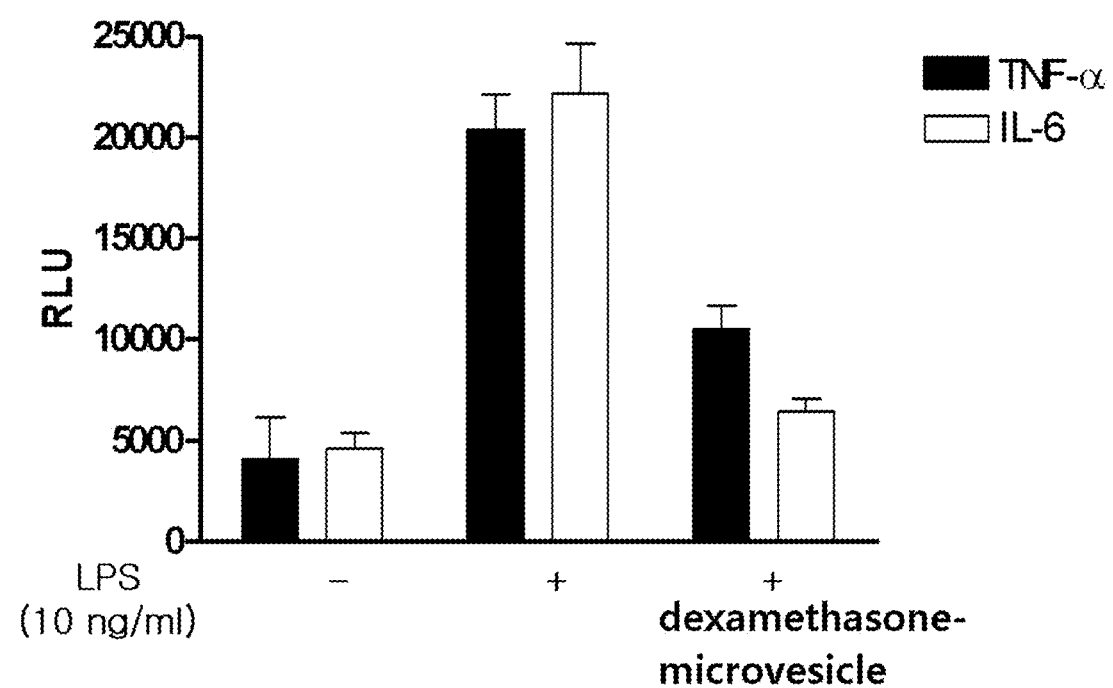
FIG. 20 is a graph showing levels of TNF-α and IL-6 secreted from cells after an anti-inflammatory drug is delivered to the cells by nucleated cell-derived microvesicles.

FIG. 20 shows RLU (relative light units) after color development, illustrating relative levels of the pro-inflammatory cytokines TNF-α and IL-6. In the graph, black and white bars are respectively responsible for TNF-α and IL-6 levels in the absence of LPS (−) and presence of 10 ng/ml LPS (+).

As can be seen in FIG. 20, neither TNF-α nor IL-6 were secreted in the absence of LPS because of the absence of an inflammatory response. In contrast, treatment with LPS induced an inflammatory response to increase the secretion of TNF-α and IL-6. In addition, when simultaneously treated with LPS and dexamethasone-loaded microvesicles, the cells showed significantly low RLU values, representing barely any secretion of cytokines. It is apparent from the data that dexamethasone-loaded microvesicles can effectively suppress the LPS-induced secretion of pro-inflammatory cytokines.

Example 16: In Vitro Drug Delivery and Cell-Specific Delivery by Monocyte-Derived Microvesicles In 24-well plates was placed cover glass coated with 0.1% gelatin to which HUVEC was then seeded at a density of 1×10$^4$ cells/cover glass, followed by incubation for 12 hours. The cells were treated for 16 hours with or without 10 ng/ml TNF-α. As stated above, TNF-α induces HUVEC to increase the expression of cell adhesion molecules, such as ICAM-1, VCAM-1 and E-selectin, on the plasma membrane. The cell adhesion molecules interact with other cell adhesion molecules such as those present in monocytes and macrophages, identified as LFA-1 and Mac-1, allowing vascular endothelial cells to bind to monocytes and macrophages.

The cells were washed with PBS and 500 μl of a medium was added to each well. Subsequently, the cells were incubated with 5 μg/ml doxorubicin-loaded microvesicles which were generated from monocytes as in Example 9. Again, the cells were washed with PBS, and 500 μl of a serum-free medium was added to each well before incubation for 30 min with 5 μM Cell Tracker (Invitrogen, No. C2925).

Again, the cells were washed with PBS, and incubated for 30 min in 500 μl of a serum-supplemented medium in each well. The cover glass was fixed for 10 min with 500 μl of 4% paraformaldehyde in each well and observed under a confocal microscope. The results are given in FIG. 21.

Figure 21:
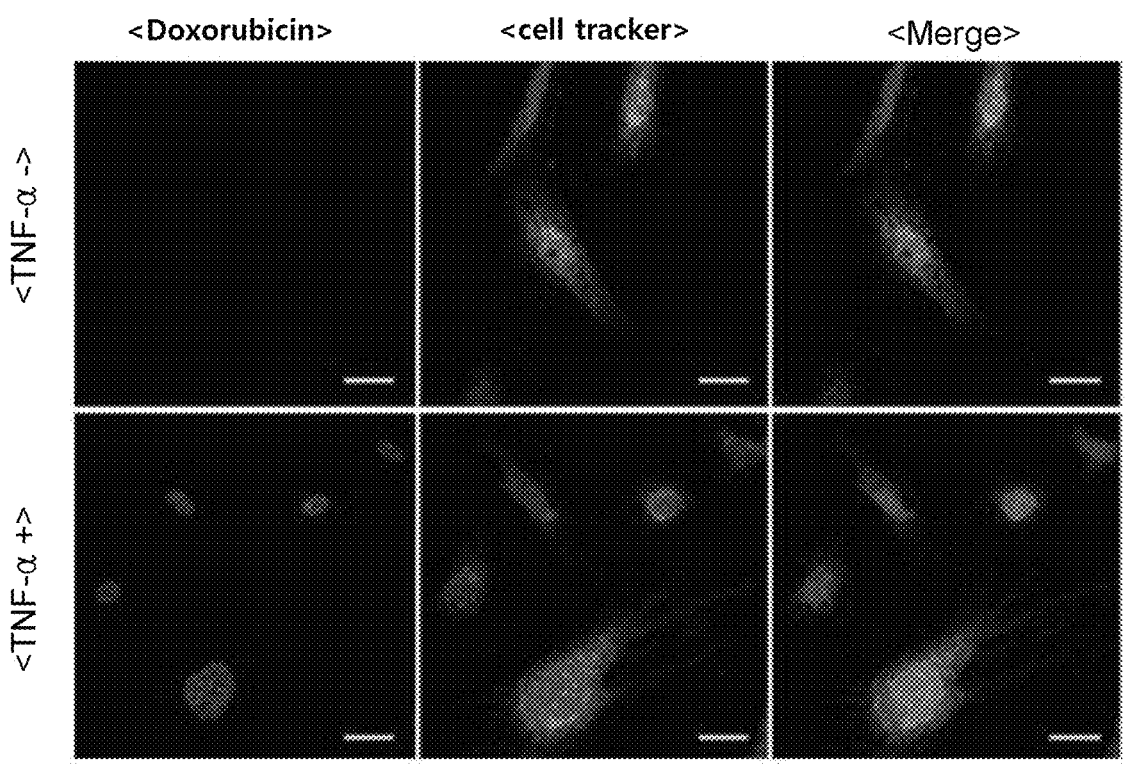
FIG. 21 is of photographs TNF-α-treated HUVEC cells after doxorubicin is delivered to the cells by nucleated cell-derived, doxorubicin-loaded microvesicles.

When HUVEC was treated with TNF-α, as seen in FIG. 21, the red fluorescence of doxorubicin was detected at the positions where the green fluorescence of the cells was emitted. These results indicate that the doxorubicin loaded to the microvesicles was delivered to the nuclei of HUVEC cells. In contrast, no doxorubicin was observed in HUVEC treated without TNF-α.

Since only a limited number of cells can be monitored with a microscope, doxorubicin delivered to all of the cells tested was quantitatively analyzed using FACS (Fluorescence Activated Cell Sorting).

Microvesicles loaded with or without doxorubicin were generated from monocytes in the same manner as in Example 9 and Example 1, respectively.

HUVEC cells were seeded at a density of 1×10$^4$ cells/well in 24-well plates coated with 0.1% gelatin and incubated for 12 hours and then for an additional 16 hours in the presence of 10 ng/ml TNF-α. The cells were washed with PBS and 500 μl of a medium was added to each well. Subsequently, the cells were incubated for 1 hour with 5 μg/ml doxorubicin-loaded or doxorubicin-free microvesicles which were generated as above. Again, the cells were washed with PBS, and detached by treatment with 100 μl of 1× TE (trypsin-EDTA) buffer at 37° C. for 5 min. To each well was added 200 μl of PBS before FACS analysis. The results are given in FIG. 22.

Figure 22:
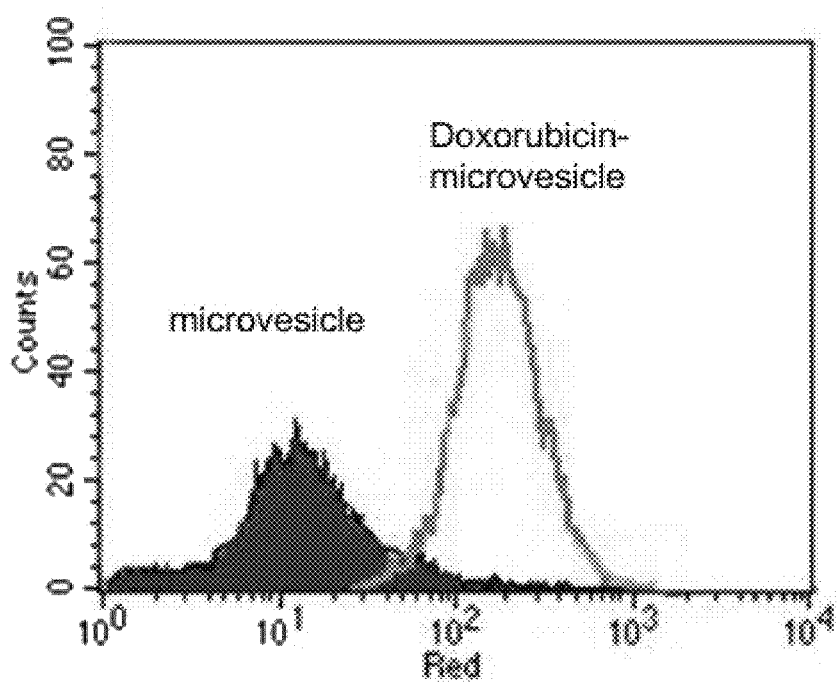
FIG. 22 is a graph showing the specific delivery of doxorubicin to TNF-α-treated HUVEC cells by nucleated cell-derived, doxorubicin-loaded microvesicles.
Figure 22:
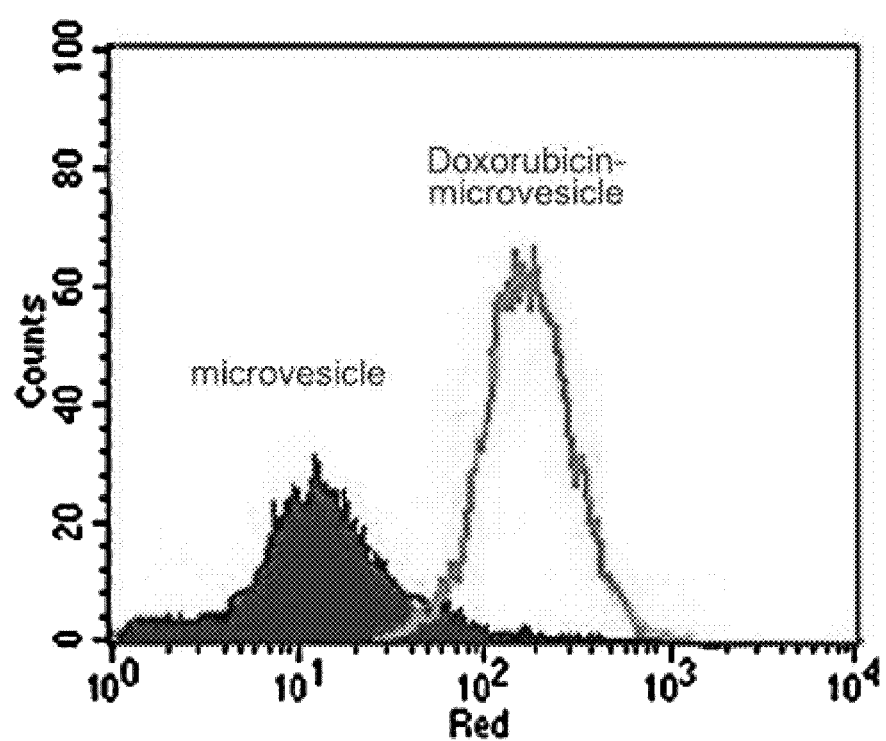

In FIG. 22, 'red' on the X-axis means the relative fluorescent intensity of doxorubicin and 'counts' on the Y-axis means the number of cells. In addition, the red and the violet graph show cell counts versus the red fluorescent intensity generated from the cells treated with microvesicles loaded with or without doxorubicin, respectively.

As shown in FIG. 22, the red fluorescent intensity of the cells treated with microvesicles void of doxorubicin were measured to have approximately 1.1×10$^1$. When treated with microvesicles loaded with doxorubicin, the red fluorescent intensity of the cells were detected at approximately 1.2× 10$^2$, which is an increase of ten or higher times. Consequently, doxorubicin was certainly delivered to cells by microvesicles.

HUVEC cells were seeded at a density of 3×10$^4$ cells/well into 24-well plates coated with 0.1% gelatin and incubated for 12 hours in 96-well plates, followed by incubation for an additional 16 hours in the presence or absence of 10 ng/ml TNF-α. The cells were washed with PBS, suspended in 100 μl of a medium in each well and treated for min with 0, 1, 2, and 5 μg/ml doxorubicin-loaded microvesicles generated from monocytes in the same manner as in Example 6. Then, the cells were washed with PBS and cultured for 24 hours in 500 μl of a fresh medium. Afterwards, the cells were washed again with PBS and stained with 1 μM calcein AM dye. Images were taken under a fluorescence microscope and viable cells were counted.

Figure 23:
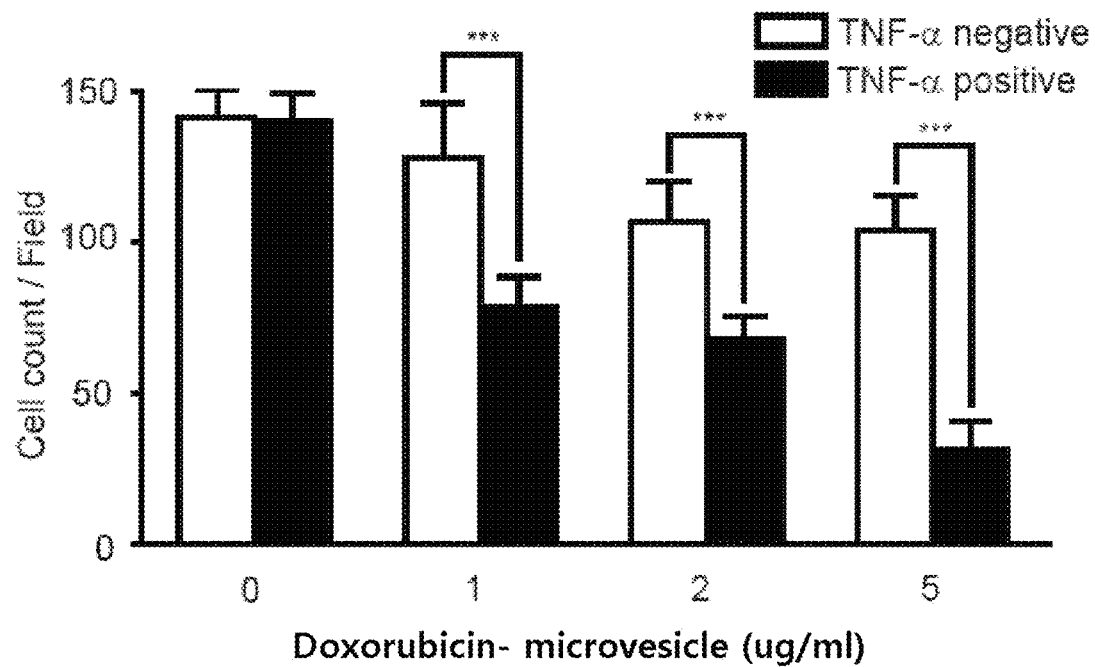
FIG. 23 is a graph showing the cell death of TNF-α-treated HUVEC cells as a result of the specific delivery of doxorubicin by nucleated cell-derived, doxorubicin-loaded microvesicles.

FIG. 23 shows 'cell counts' of the stained cells, which means the numbers of viable cells.

As can be seen in FIG. 23, HUVEC experienced cell death in a dose-dependent behavior when treated with TNF-α, but almost no apoptosis was induced in the cells treated in the absence of TNF-α.

From the results, it is apparent that cell death can be induced by the doxorubicin loaded to the microvesicle and at higher intensity in the cells treated with TNF-α, that is, activated cells.

HUVEC cells were seeded at a density of 3×10$^4$ cells/well into 24-well plates coated with 0.1% gelatin and incubated for 12 hours in 96-well plates, followed by incubation for an additional 16 hours in the presence or absence of 10 ng/ml TNF-α. The cells were washed with PBS, suspended in 100 μl of a medium in each well and treated for 20 min with 0, 1, 2, and 5 μg/ml microvesicles which were generated from monocytes in the same manner as in Example 9 with the exception that 5-fluorouracil, gemcitabine or carboplatin, instead of doxorubicin, was used. Then, the cells were washed with PBS and cultured for 24 hours in 500 μl of a fresh medium. Afterwards, the cells were washed again with PBS and stained with 1 μM calcein AM dye. Images were taken under a fluorescence microscope and viable cells were counted.

Figure 24:
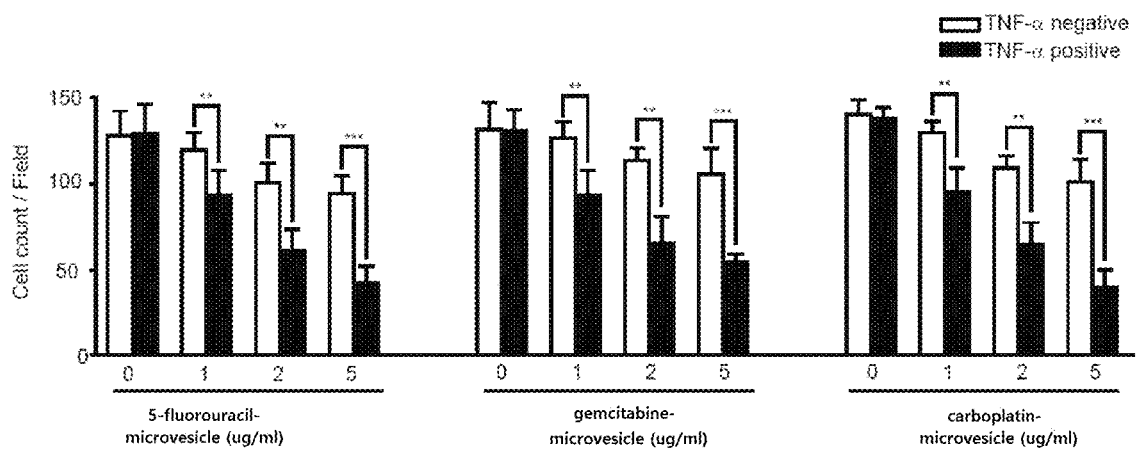
FIG. 24 is of graphs showing the cell death of cells as a result of the delivery of various drugs by nucleated cell-derived microvesicles.

FIG. 24 shows 'cell counts' of the stained cells, which means the numbers of viable cells.

As can be seen in FIG. 24, HUVEC experienced cell death in a dose-dependent behavior when treated with TNF-α, but almost no cell death was induced in the cells treated in the absence of TNF-α.

To confirm the important role of cell adhesion molecules in the activation of monocyte-derived microvesicles, HT1080 cells in which the expression of ICAM-1 was upregulated or downregulated by transformation with sense ICAM-1 or antisense ICAM-1, respectively, were prepared.

The cells were treated at 37° C. for 30 min with 0.1, 0.5 and 1 μg/ml microvesicles which were generated from monocytes in the same manner as in Example 9. Then, the cells were washed with PBS and cultured for 24 hours in a fresh medium. Afterwards, the cells were washed again with PBS and stained with 1 μM calcein AM dye. Images were taken under a fluorescence microscope and viable cells were counted.

Figure 25:
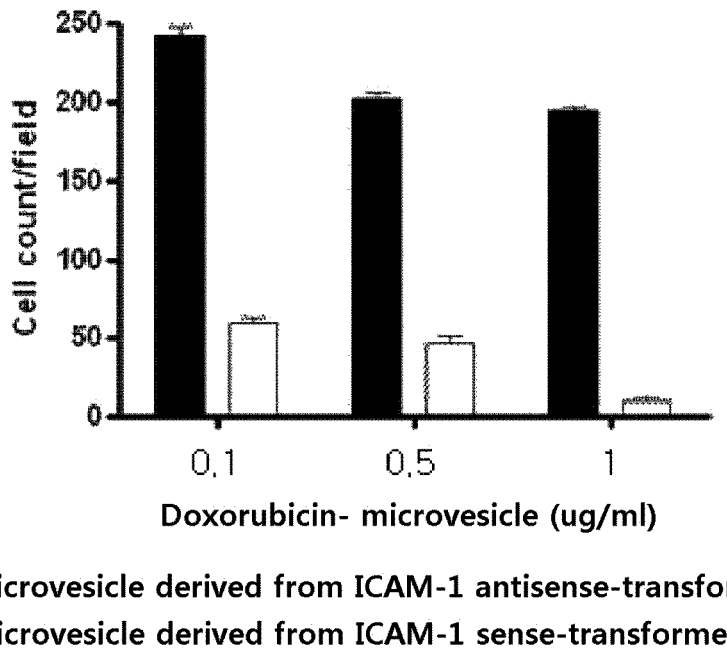
FIG. 25 is a graph showing the effect of cells overexpressing or lacking ICAM-1 as a result of the delivery of doxorubicin by nucleated cell-derived, doxorubicin-microvesicles.

FIG. 25 shows counts of the stained cells measured in the images.

As can be seen in FIG. 25, the number of the HT1080 cells which were induced to experience cell death was greater when they expressed ICAM-1 than when they did not express ICAM-1. This result indicates that the microvesicles derived from monocytes have LFA-1 proteins exposed on the surface thereof, like monocytes, and can deliver their loads more effectively to ICAM-1-overexpressed HT1080 cells through the specific interaction between LFA-1 and ICAM-1.

Consequently, monocyte-derived, anticancer drug-loaded microvesicles with a cell adhesion molecule such as LFA-1 expressed thereon can bind specifically to cells which express a cell adhesion molecule such as ICAM-1 thanks to the interaction between the cell adhesion molecules so that the anticancer drug load can be delivered to the cells, inducing cell death.

Example 17: Induction of Toxicity in Cells Under Division by Monocyte-Derived Microvesicles HUVEC was inoculated at a density of $1\times10^5$ cells into a 35 mm culture plate coated with 0.1% gelatin and grown for 12 hours to full confluency. Subsequently, cells were scratched using a 200 p tip and incubated for 16 hours in the presence of 10 ng/ml TNF-α.

The cells were washed with PBS and 1 ml of a medium was added to each well. Subsequently, the cells were cultured for 20 min with 5 μg/ml microvesicles which were generated from monocytes as in Example 9. The cells were then washed with PBS and cultured for 24 hours in 1 mL of a fresh medium. Again, the cells were washed with PBS and stained with 1 μM calcein AM dye. Images were taken using a fluorescence microscope and are given in FIG. 26.

Figure 26:
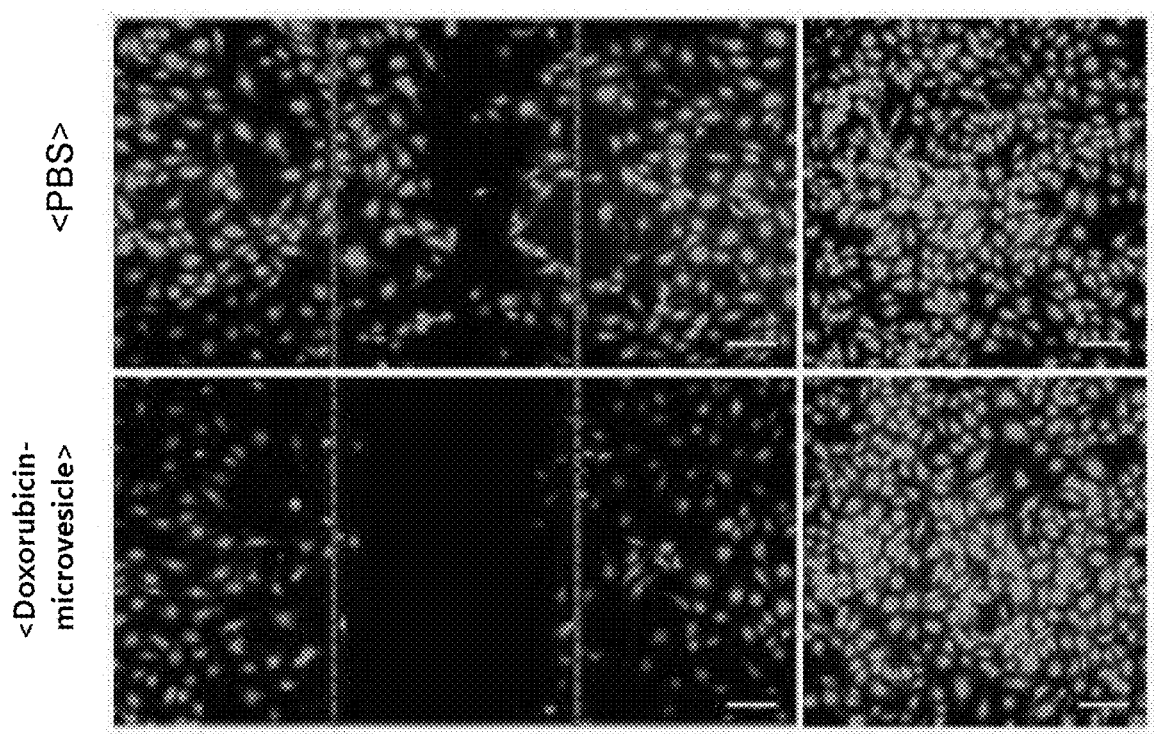
FIG. 26 is of photographs the specific delivery of doxorubicin to dividing cells by nucleated cell-derived, doxorubicin-loaded microvesicles.

In FIG. 26, viable cells appear green with the presentation of scratched portions in red. When grown to confluency, HUVEC cells do not undergo division due to contact inhibition. Given a space by scratching, the cells start to divide and migrate to the void.

As can be seen in FIG. 26, the cells which were treated with no substance had divided and migrated to the voids so that they were observed to be filled with green on a fluorescence microscope. However, when the cells were treated with doxorubicin-loaded microvesicles, the scratched portions still remained void. In addition, no changes were detected in scratch-free, confluent regions even though doxorubicin-loaded microvesicles were applied thereto. From the data, it is apparent that doxorubicin-loaded microvesicles act specifically on cells under division.

Example 18: In Vivo Induction of Cell Death in Cancer by Macrophage-Derived, Doxorubicin-Loaded Microvesicles Mouse colon 26 cell line was subcutaneously injected at a dose of $1\times10^6$ cells into mice [Cancer Res. 57; 1625-1629 (1997)] and cultured for 5 days.

Microvesicles devoid of doxorubicin were generated from macrophages by extrusion in a manner similar to that of Example 1. Separately, microvesicles loaded with 3 μg of doxorubicin (doxorubicin-microvesicles) were generated from macrophages suspended in a 400 μg/ml doxorubicin solution by extrusion in a manner similar to that of Example 9.

Five days after the subcutaneous injection, PBS, a PBS solution containing 10 μg of the extruded microvesicles (microvesicle), a PBS solution containing 2 μg of extruded microvesicles loaded with 0.6 μg of doxorubicin (doxorubicin-microvesicle (2)), or a PBS solution containing 10 μg of extruded microvesicles loaded with 3 μg of doxorubicin (doxorubicin-microvesicle (10)) was injected at a dose of 100 μl once a day via the tail vein into mouse groups, each consisting of 10. The sizes of cancer tissue were monitored once every two days. The volume of cancer tissue was calculated by the equation $v=1s^2/2$ wherein (1) is a length of the longest axis of a tumor and (s) is a length of the axis perpendicular to the longest axis.

Figure 27:
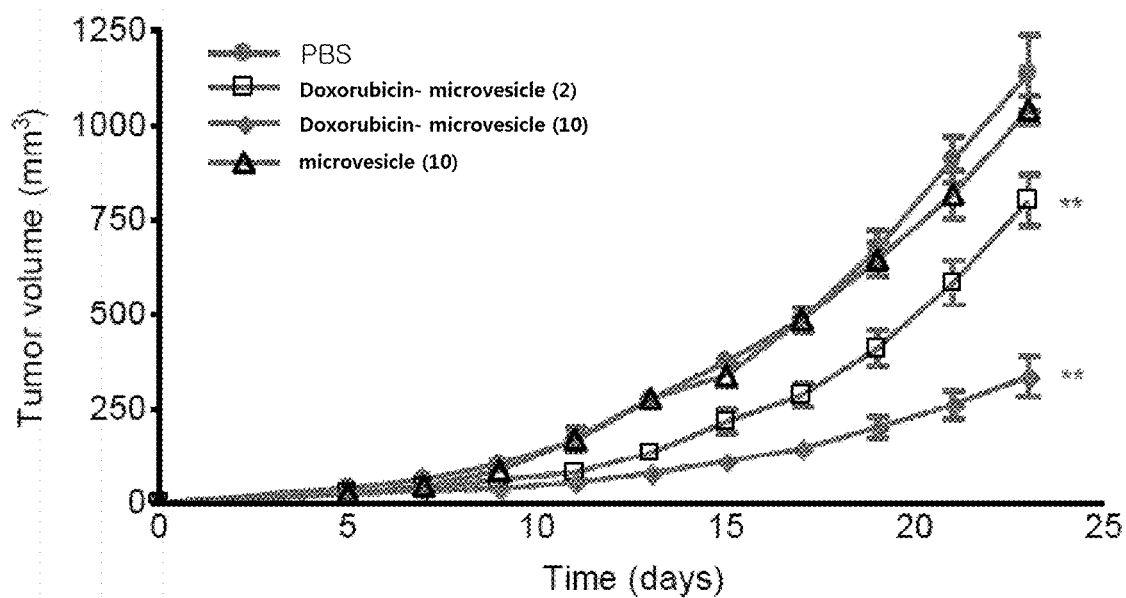
FIG. 27 is a graph showing the inhibition of cancer cell growth after nucleated cell-derived, doxorubicin-loaded microvesicles are administered to mice.

After the cancer cells were implanted subcutaneously, the sizes of the cancer tissue were measured and the measurements are shown in FIG. 27.

As can be seen in FIG. 27, the lowest cancer growth was found when the extruded microvesicles loaded with doxorubicin were injected at a dose of 10 μg every day. The microvesicles devoid of doxorubicin had no influence on the growth of cancer tissues.

This result indicates that the anticancer drug doxorubicin can be delivered to cancer tissue by the microvesicles.

Example 19: In Vivo Mechanism of Cancer Cell Death by Macrophage-Derived, Doxorubicin-Loaded Microvesicles The cancer tissue excised from mice treated with PBS or doxorubicin-microvesicles in Example 18 were fixed for 24 hours in 4% paraformaldehyde. For dehydration, the fixed cancer tissue was immersed once in 70% ethanol, four times in 95% ethanol, three times in 100% ethanol, and three times in 100% xylene, each time for one hour in all cases. Thereafter, the tissues were embedded in paraffin, cut into sections 4 μm thick, and attached onto slide glass. The paraffin was melted by incubation at 60° C. for one hour. For hydration, the tissues were immersed three times in 100% xylene, four times in 100% ethanol, and three times in 95% ethanol, each time for one min in all cases, followed by storage for 5 min in flowing water.

After the hydration, the tissues were subjected to immunohistochemistry. In this regard, antigen retrieval was performed using a microwave method. The tissues were placed in 10 mM sodium citrate buffer (Sigma, No. S4641) and irradiated three times, each for five min, with microwaves. The tissues were cooled with flowing water and blocked for 2 hours with TBS (Tris Buffered Saline) containing 5% horse serum and 0.02% Triton X-100. An antibody (Santa-Cruz, No. SC1506) recognizing the endothelial marker CD31 was mixed at a ratio of 1:200 with TBS containing 5% horse serum and 0.02% Triton X-100, followed by incubation at 4° C. for 12 hours. The tissues were washed three times with TBS containing 0.02% Triton X-100 and incubated at room temperature for 1 hour with a green fluorescent Alexa 488-conjugated secondary antibody. They were washed three times with TBS containing 0.02% Triton X-100, and stained for 10 min with 5 μM host dye. The tissues were washed five times with TBS and the cover glass was underlayered with slide glass and observed under a confocal microscope. In the images, green-stained regions were measured.

Figure 28:
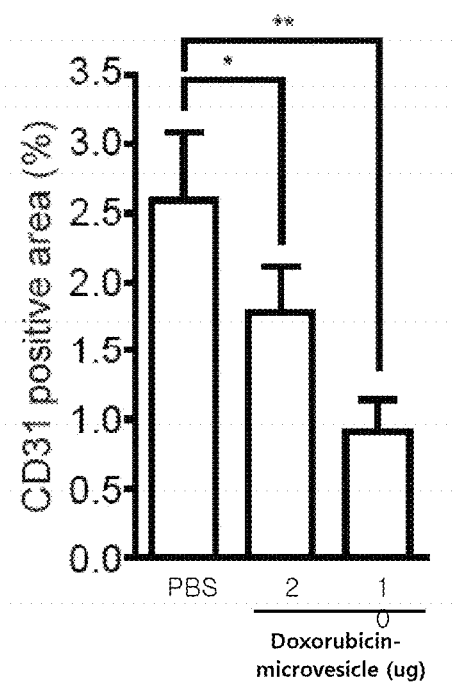
FIG. 28 is a graph showing the area of the endothelial marker CD31 in cancer tissue after treatment with nucleated cell-derived, doxorubicin-loaded microvesicles.

In the graph of FIG. 28, the vascular regions are quantitatively analyzed on images. Green areas (CD31 positive areas responsible for blood vessels) are scaled on the Y-axis in the graph of FIG. 28. Blood vessels were analyzed in 10 images in total. As shown in FIG. 28, the area of blood vessels was reduced in a dose-dependent manner by the microvesicles.

To examine whether the disruption of blood vessels reduces the division cycle number of cancer cells immunohistochemistry was performed on the hydrated tissues. In this context, the tissues were placed in 10 mM sodium citrate buffer and irradiated three times, each time for 5 min, with microwaves for antigen retrieval. The tissues were cooled with flowing water and blocked for 2 hours with TBS (Tris Buffered Saline) containing 5% horse serum and 0.02% Triton X-100. An antibody (Upstate, No. 06-570) recognizing the cell division marker phosphor-histone 3 (PH-3) was mixed at a ratio of 1:200 with TBS containing 5% horse serum and 0.02% Triton X-100, followed by incubation at 4° C. for 12 hours. The tissues were washed three times with TBS containing 0.02% Triton X-100 and incubated at room temperature for 1 hour with a green fluorescent Alexa 488-conjugated secondary antibody. They were washed three times with TBS containing 0.02% Triton X-100, and stained for 10 min with 5 μM host dye. The tissues were washed five times with TBS and the cover glass was underlayered with slide glass and observed under a confocal microscope.

Figure 29:
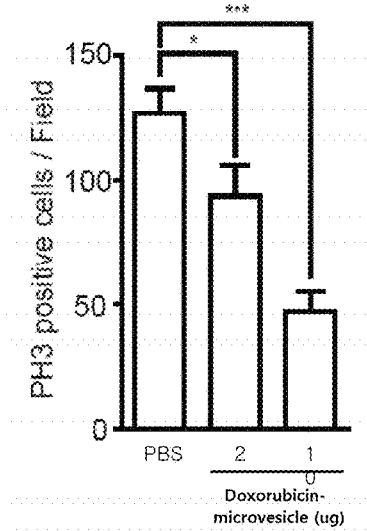
FIG. 29 is a graph showing counts of the cells stained with the cell proliferation marker PH-3 in cancer tissue after treatment with nucleated cell-derived, doxorubicin-loaded microvesicles.

In the graph of FIG. 29, the dividing cells are quantitatively analyzed on the images. Green cell counts (PH3 positive cells) are scaled on the Y-axis in the graph of FIG. 29. Cells were counted in 10 images in total. As shown in FIG. 29, the counts of dividing cells were reduced in a dose-dependent manner by the microvesicles.

Taken together, the data demonstrate that doxorubicin-loaded microvesicles induce the disruption of vascular endothelial cells in cancer tissue, thereby reducing the division of cancer cells.

Example 20: Delivery of Doxorubicin to In Vivo Cancer Tissue Blood Vessels by Macrophage-Derived, Doxorubicin-Loaded Microvesicles The mouse colon 26 cell line used in Example 18 was subcutaneously injected at a dose of $1 \times 10^6$ cells into mice and cultured for 5 days.

Microvesicles loaded with 3 μg of doxorubicin were generated from a suspension of macrophages in a 400 μg/ml doxorubicin solution by extrusion in a similar manner to that of Example 9 (doxorubicin-microvesicle).

After cultivation for 10 days, PBS, PBS containing 100 μg of the extruded microvesicles (doxorubicin-microvesicle), or PBS containing 30 μg of doxorubicin was injected at a dose of 100 μl into mice via the tail vein.

Six hours after the injection, cancer tissue, the spleen and the heart were excised from the mice and fixed for 24 hours in 4% paraformaldehyde. For dehydration, the fixed tissues were immersed once in 70% ethanol, four times in 95% ethanol, three times in 100% ethanol, and three times in 100% xylene, each time for one hour in all cases. Thereafter, the tissues were embedded in paraffin, cut into sections 4 μm thick, and attached onto slide glass. The paraffin was melted by incubation at 60° C. for one hour. For hydration, the tissues were immersed three times in 100% xylene, four times in 100% ethanol, and three times in 95% ethanol, each time for one min in all cases, followed by storage for 5 min in flowing water.

After the hydration, the tissues were subjected to immunohistochemistry to examine whether doxorubicin was delivered to each tissue. In this regard, antigen retrieval was performed using a microwave method. The tissues were placed in 10 mM sodium citrate buffer and irradiated three times, each for five min, with microwaves. The tissues were cooled in flowing water and blocked for 2 hours with TBS containing 5% horse serum and 0.02% Triton X-100. An antibody (SantaCruz, No. SC1506) recognizing the endothelial marker CD31 was mixed at a ratio of 1:200 with TBS containing 5% horse serum and 0.02% Triton X-100, followed by incubation at 4° C. for 12 hours. The tissues were washed three times with TBS containing 0.02% Triton X-100 and incubated at room temperature for 1 hour with a green fluorescent Alexa 488-conjugated secondary antibody. They were washed five times with TBS and the cover glass was underlayered with slide glass and observed under a confocal microscope.

Figure 30:
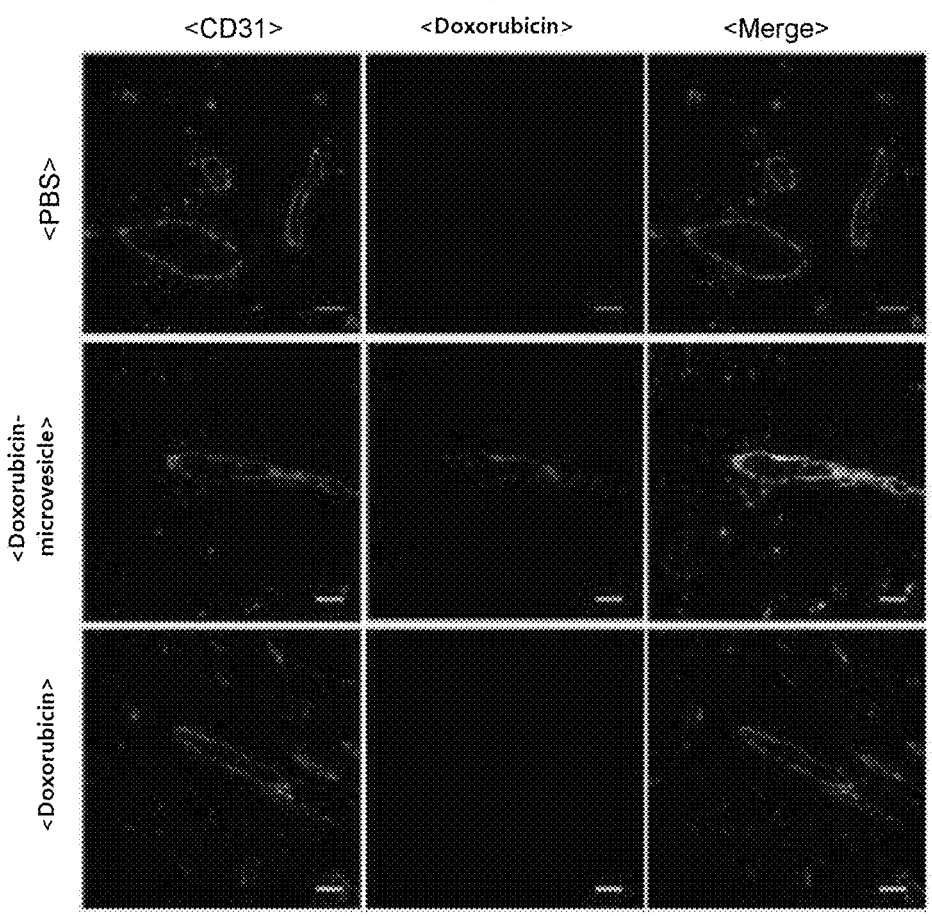
FIG. 30 is of photographs showing the delivery of doxorubicin to cancer tissue by nucleated cell-derived, doxorubicin-loaded microvesicles.
Figure 31:
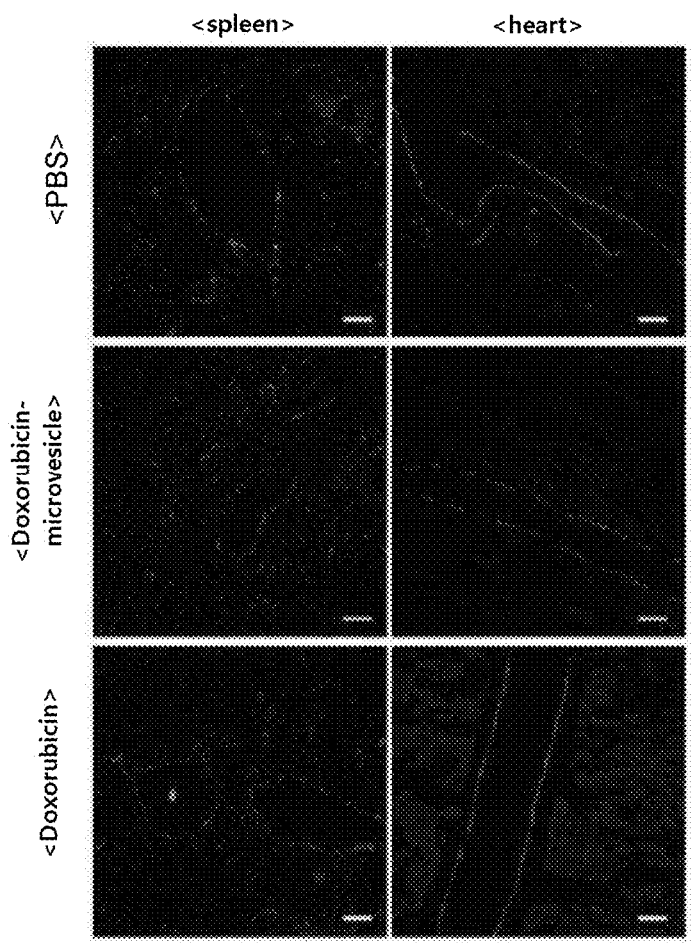
FIG. 31 is of photographs showing the presence of doxorubicin in the spleen and the heart after nucleated cell-derived, doxorubicin-loaded microvesicles and doxorubicin are administered to mice.

FIG. 30 shows images taken from cancer tissue while FIG. 31 is of images taken from the spleen and the heart. In these images, blood vessels appear green with doxorubicin being represented by red.

As can be seen in FIG. 30, doxorubicin is delivered to cancer blood vessels only via microvesicles, but cannot by itself be delivered.

From these results, it is obvious that doxorubicin loaded to macrophage-derived microvesicles can be delivered to vascular cells of cancer tissues.

Also it is apparent from the data of FIG. 31 that doxorubicin alone is delivered in a large amount to the heart, but when doxorubicin is loaded to the microvesicles, the amount thereof delivered to the heart is significantly reduced.

This result indicates that the cardiotoxicity of doxorubicin can be reduced by the microvesicles of the present invention.

Example 21: Induction of In Vivo Cancer Cell Death by Macrophage-Derived, Doxorubicin-Loaded Microvesicles, and Comparison with Doxorubicin The mouse colon 26 cell line used in Example 18 was subcutaneously injected at a dose of $1 \times 10^6$ cells into mice and cultured for 5 days.

Microvesicles loaded with 3 µg of doxorubicin were generated from a suspension of macrophages in a 400 µg/ml doxorubicin solution by extrusion in a similar manner to that of Example 9 (doxorubicin-microvesicle).

After cultivation for 5 days, PBS, PBS containing 10 µg of the extruded microvesicles loaded with 3 µg of doxorubicin (doxorubicin-microvesicle), or PBS containing 3, 15 or 60 µg of doxorubicin was injected at a dose of 100 µl once every day via the tail vein into mouse groups, each consisting of 5. The volume of cancer tissue was monitored once every two days. The tumor volume was calculated by the equation $v = ls^2/2$ wherein (1) is a length of the longest axis of a tumor and (s) is a length of the axis perpendicular to the longest axis.

Figure 32:
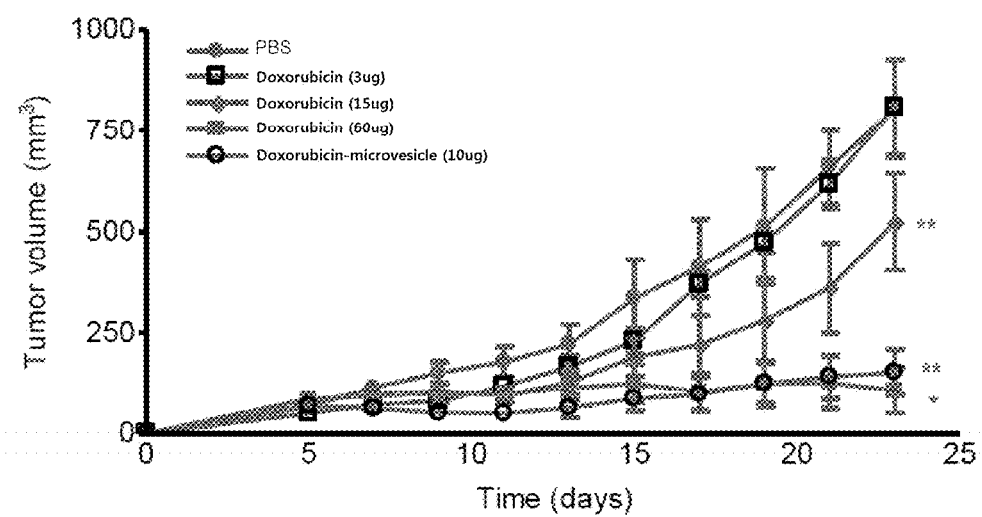
FIG. 32 is a graph showing the growth of cancer tissues according to the concentration of doxorubicin-loaded microvesicles and doxorubicin.

After the cancer cells were implanted subcutaneously, the sizes of the cancer tissue were measured and the measurements are shown in FIG. 32. As shown, the lowest cancer growth was found when the extruded microvesicles loaded with doxorubicin were injected at a dose of 10 µg every day. The microvesicles devoid of doxorubicin had no influences on the growth of cancer tissues. When administered alone, the dose of doxorubicin which exhibited the same therapeutic effect as in the microvesicles loaded with doxorubicin was measured to be 60 µg, which was 20-fold higher than the load of doxorubicin on the microvesicles.

Figure 33:
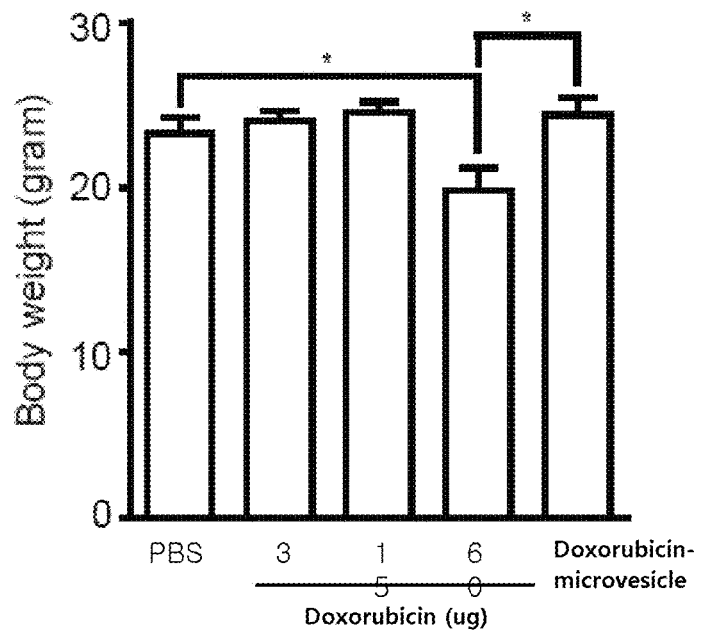
FIG. 33 is a graph showing weights of mice after treatment with doxorubicin-loaded microvesicles and doxorubicin.

FIG. 33 is a graph showing body weights of the mouse groups, each consisting of five.

As seen in FIG. 33, there were no significant changes in body weight in the mice administered every day with 10 µg of the doxorubicin-microvesicle and the PBS control. However, the body weight of the mice administered with 60 µg of doxorubicin was reduced significantly.

Mice were anesthetized by abdominal injection of 150 µL of an anesthetic comprising a mixture of 1:3:6 ketamine:rumpon:PBS, and blood samples were taken from the heart and placed in tubes containing an anti-coagulant agent. A mixture of 10 µL of blood and 90 µL of 1% HCl was stored at room temperature for 7 min, and after 10 µL of the mixture was put into a hematocytometer, and white cells were counted.

Figure 34:
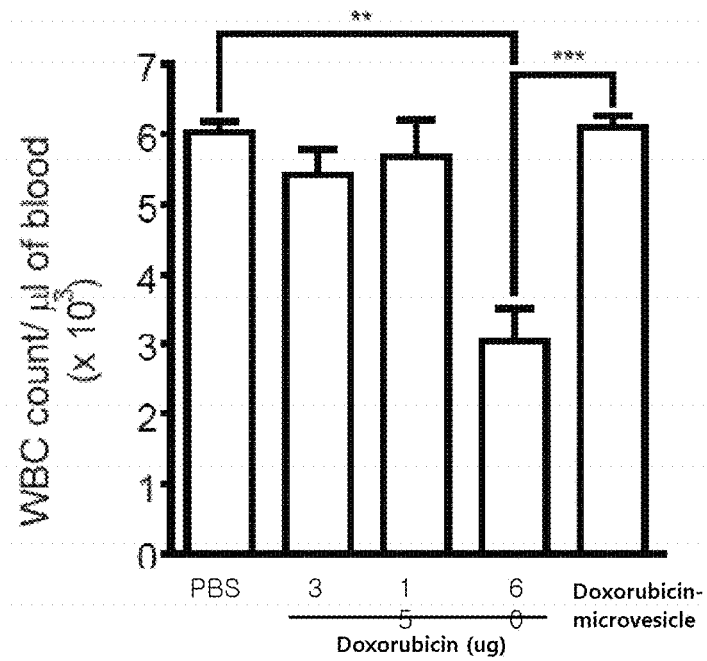
FIG. 34 is a graph showing white blood cell counts in blood after mice are treated with doxorubicin-loaded microvesicles and doxorubicin.

FIG. 34 shows counts of leukocytes present in blood as measured by this process.

As is apparent from the data of FIG. 34, white blood cell counts were not decreased in the mice injected every day with 10 µg of doxorubicin-loaded microvesicles while the white blood cell count of the mice injected with 60 µg of doxorubicin was reduced by at least 50%, compared to the control.

This result implies that the use of microvesicles reduces the adverse effects of doxorubicin.

Example 22: Induction of In Vivo Cancer Cell Death by Macrophage-Derived, Doxorubicin-Loaded Microvesicles and Role of Membrane Proteins The mouse colon 26 cell line used in Example 18 was subcutaneously injected at a dose of $1 \times 10^6$ cells into mice and cultured for 5 days.

Microvesicles loaded with 3 µg of doxorubicin were generated from a suspension of macrophages in a 400 µg/ml doxorubicin solution by extrusion in a manner similar to that of Example 9 (doxorubicin-extrusion microvesicle). The doxorubicin-loaded microvesicles were trypsinized to remove membrane proteins therefrom (doxorubicin-extrusion microvesicle (T)). Separately, doxorubicin-loaded microvesicles were prepared using sonication (doxorubisin-sonication microvesicle).

After cultivation for 5 days, PBS, PBS containing 10 µg of the extruded microvesicles loaded with 3 µg of doxorubicin, PBS containing 10 µg of the doxorubicin-extrusion microvesicle (T), or PBS containing 10 µg of the sonicated microvesicles loaded with 3.6 µg of doxorubicin were injected at a dose of 100 µl once every day via the tail vein into mouse groups, each consisting of 5. The volume of cancer tissues were monitored once every two days. The tumor volume was calculated by the equation $v = ls^2/2$ wherein (1) is a length of the longest axis of a tumor and (s) is a length of the axis perpendicular to the longest axis.

Figure 35:
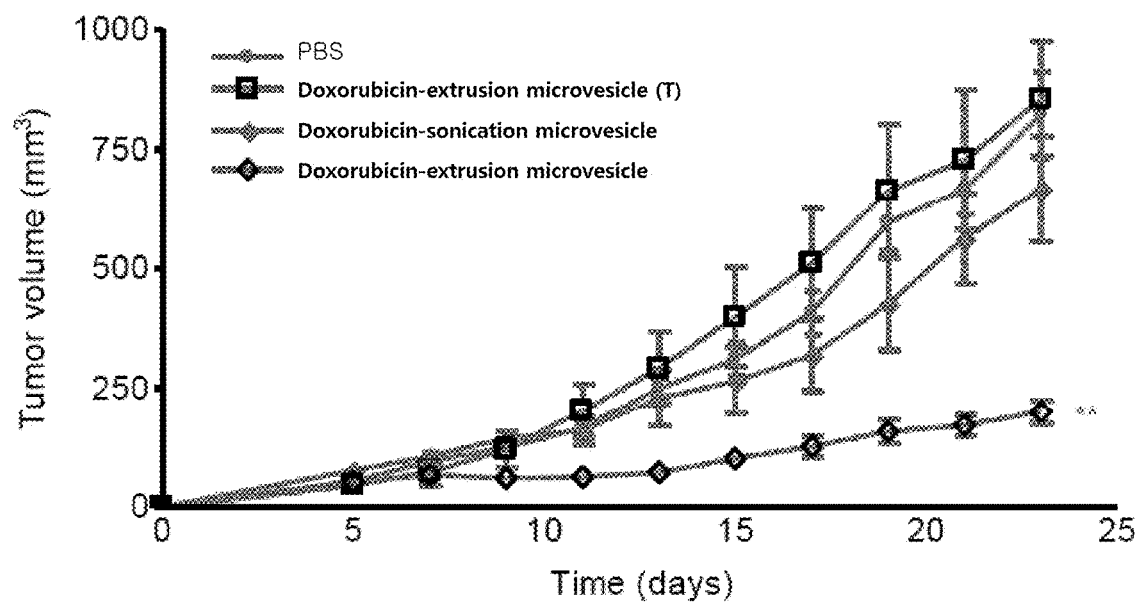
FIG. 35 is a graph showing the role of membrane proteins and topology in the performance of the microvesicles.

After the cancer cells were implanted subcutaneously, the sizes of the cancer tissue were measured and the measurements are shown in FIG. 35.

As can be seen in FIG. 35, the lowest cancer growth was found when the extruded microvesicles loaded with doxorubicin were injected at a dose of 10 µg every day. In contrast, the microvesicles trypsinized to remove membrane protein therefrom and the sonicated microvesicles with a change in the topology of membrane proteins had no significant influence on the growth of cancer tissues.

This result indicates that membrane proteins and the topology of membrane proteins play an important role in the activity of the microvesicles.

Example 23: Induction of In Vivo Cancer Cell Death by Macrophage-Derived, Anticancer Drug-Loaded Microvesicles Microvesicles loaded with 5-fluorouracil, gemcitabine, carboplatin or EGCG were generated from monocytes in the same manner as in Example 9 with the exception that 5-fluorouracil, gemcitabine, carboplatin, or EGCG (Epigallocatechin gallate), instead of doxorubicin, was used.

The mouse colon 26 cell line used in Example 18 was subcutaneously injected at a dose of $1 \times 10^6$ cells into mice and cultured for 5 days. Thereafter, PBS containing 15 µg of microvesicles loaded with 5-fluoreuracil, or PBS containing 10 µg of microvesicles loaded with gemcitabine, carboplatin or EGCG was injected at a dose of 100 µl once every day via the tail vein into mouse groups. The volume of cancer tissue was monitored once every two days. The tumor volume was calculated by the equation $v = ls^2/2$ wherein (1) is a length of the longest axis of a tumor and (s) is a length of the axis perpendicular to the longest axis.

Figure 36:
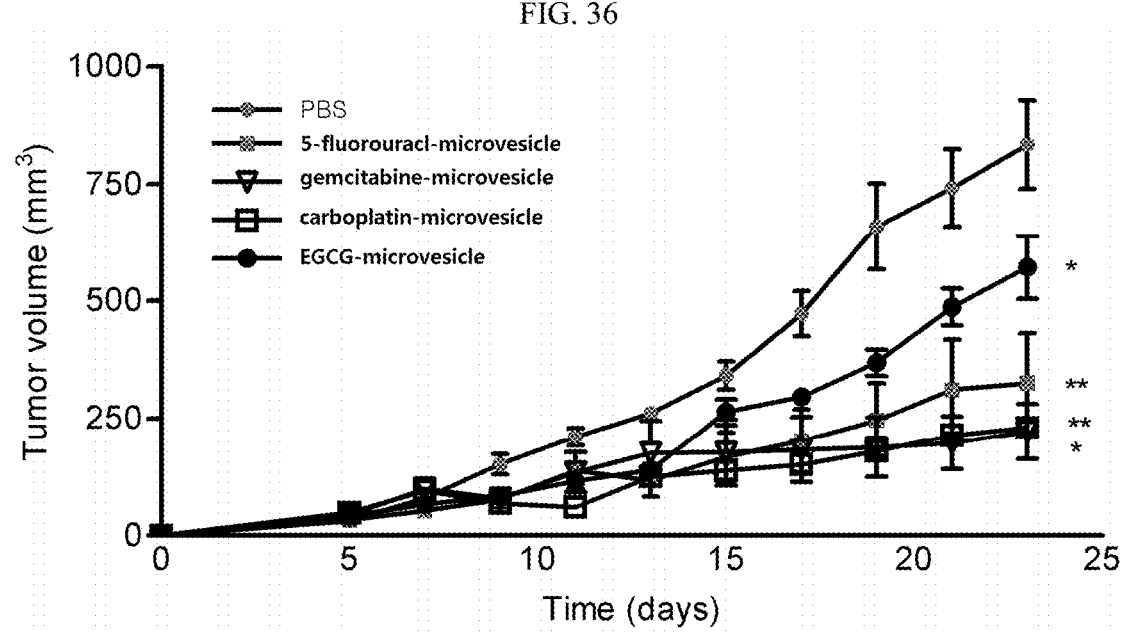
FIG. 36 is a graph showing the inhibition of the growth of cancer tissue by microvesicles loaded with various drugs.

After the cancer cells were implanted subcutaneously, the sizes of the cancer tissue were measured and the measurements are shown in FIG. 36. As can be seen in FIG. 36, the tumor was found to grow slowly when the extruded microvesicles loaded with respective drugs were injected every day.

It is apparent from the result that the microvesicles can be loaded with various drugs and promise the therapeutic effects of the drugs, e.g., anticancer effects.

Example 24: Induction of In Vivo Xenograft Lung Cancer Cell by Macrophage-Derived, Anticancer Drug-Loaded Microvesicles The human lung cancer cell line A549 in mixture with matrigel was subcutaneously injected at a dose of $2 \times 10^6$ cells into nude mice and cultured for 25 days.

Microvesicles loaded with both gemcitabine and carboplatin were generated from macrophages in a manner similar to that of Example 9, with the exception that gemcitabine and carboplatin were used simultaneously, instead of doxorubicin.

After cultivation for 25 days, PBS, PBS containing 5 μg of the extruded microvesicles loaded with the drugs, or PBS containing 20 μg of the extruded microvesicles loaded with the drug, was injected at a dose of 100 μl once every two days via the tail vein into mouse groups, each consisting of 5. The volume of cancer tissue was monitored once every two days. The tumor volume was calculated by the equation $v=ls^2/2$ wherein (1) is a length of the longest axis of a tumor and (s) is a length of the axis perpendicular to the longest axis.

Figure 37:
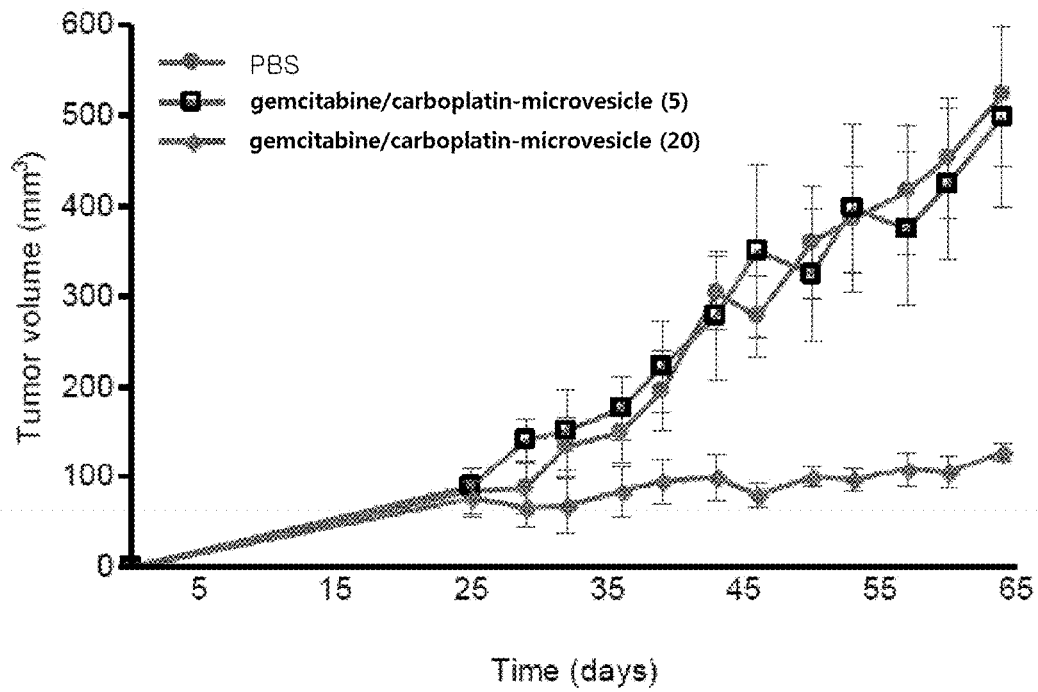
FIG. 37 is a graph showing the inhibition of the growth of human lung cancer cells by microvesicles loaded with gemcitabine and carboplatin.

After the lung cancer cells were implanted subcutaneously, the sizes of the cancer tissues were measured and the measurements are shown in FIG. 37. As can be seen in FIG. 37, the lowest cancer growth was found when the extruded microvesicles loaded with the drugs were injected at a dose of 20 μg every two days.

This result demonstrates that the anticancer drug-loaded microvesicles have therapeutic effects on the cancer tissue implanted with a human cancer cell xenograft.

Example 25: Inhibition of In Vivo Cancer Metastasis by Macrophage-Derived, Doxorubicin-Loaded Microvesicles The mouse melanoma cell line B16BL6 was injected at a dose of $2\times10^5$ cells into BNX mice via the tail vein and cultured for 3 days.

Microvesicles loaded with 3 μg of doxorubicin were generated from a suspension of macrophages in a 400 μg/ml doxorubicin solution according to the procedure of Example 9.

After cultivation for 3 days, PBS, PBS containing 2 μg of the extruded microvesicles loaded with 0.6 μg of doxorubicin (doxorubicin-microvesicle (2)), or PBS containing 10 μg of the extruded microvesicles loaded with 3 μg of doxorubicin (doxorubicin-microvesicle (10)) was injected at a dose of 100 μl once every days via the tail vein into mouse groups, each consisting of 5 mice.

Figure 38:
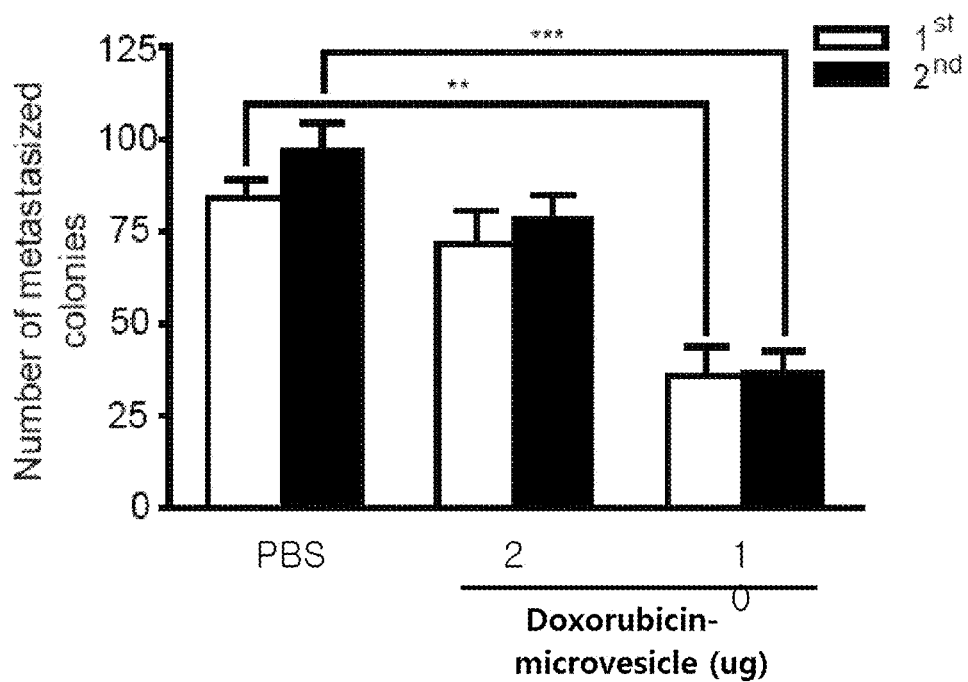
FIG. 38 is a graph showing numbers of melanoma colonies metastasized to the lung after treatment with doxorubicin-loaded microvesicles.

FIG. 38 is a graph showing numbers of melanoma colonies metastasized to the lung in each mouse group of 5. As can be seen in FIG. 38, the mice administered every day with 10 μg of the doxorubicin-loaded microvesicles were found to have the fewest melanoma colonies metastasized to the lung. This experiment was conducted in duplicate.

Melanoma cells were implanted into 10 mice, followed by the administration of the doxorubicin-loaded microvesicles. Survival rates of the mice were measured.

Figure 39:
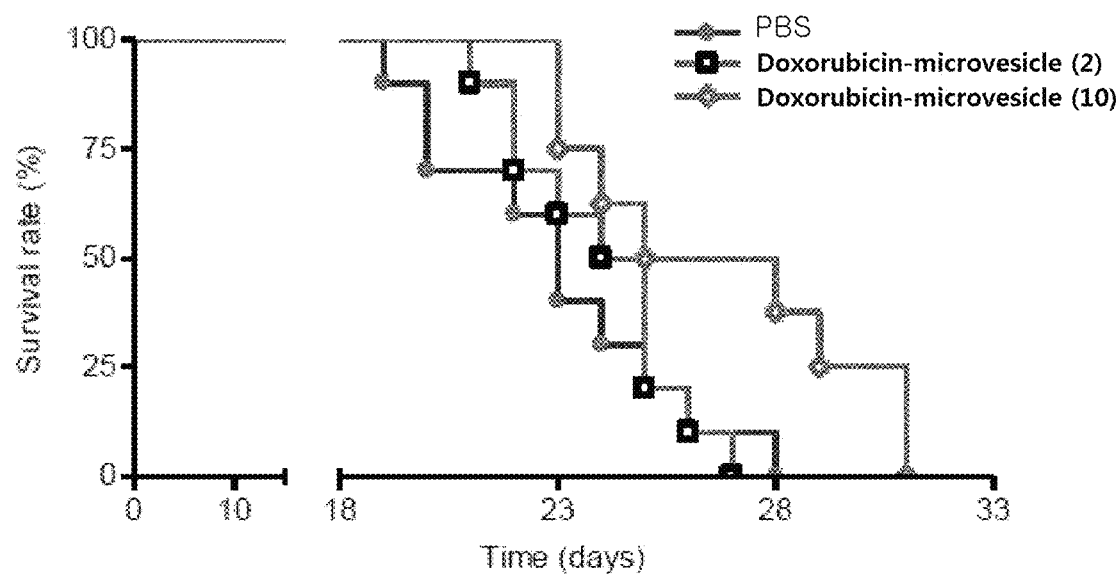
FIG. 39 is a graph showing survival rates of mice suffering from melanoma after treatment with doxorubicin-loaded microvesicles.

FIG. 39 is a graph showing the survival rates of mice. As shown in FIG. 39, the administration of 10 μg of the doxorubicin-loaded microvesicles increased the survival rate, compared to the PBS control.

It is apparent from the data that the doxorubicin-loaded microvesicles of the present invention can suppress the growth of metastasized cancer.

Example 26: Preparation of Bone Marrow-Derived Microvesicles and Drug Delivery Thereof A bone marrow aspiration was taken from the pelvic bone. In this regard, the hind limbs were excised from mice and muscle mass was removed from the limbs to give pure pelvic bones. Bone marrow cells were withdrawn from the bone using a 1 mL syringe, followed by centrifugation at 500× g. The bone marrow cells were incubated at room temperature for 10 min in RBC lysis buffer (0.15 M $NH_4Cl$, 10 mM $KHCO_3$, 0.1 mM $Na_2EDTA$, pH 7.2). After centrifugation at 500× g, the cells free of RBC were suspended in PBS. From this suspension, microvesicles were generated in a manner similar to that of Example 1.

In order to demonstrate that the bone marrow-derived microvesicles target the bone marrow, the following experiment was performed. The microvesicles were incubated for 30 min with 5 μM DiI, a red fluorescent dye. The DiI-labeled microvesicles were injected into mice via the tail vein. Six hours after the injection, bone marrow cells were taken from the mice. After the removal of red blood cells therefrom, the cells were subjected to FACS analysis.

Figure 40:
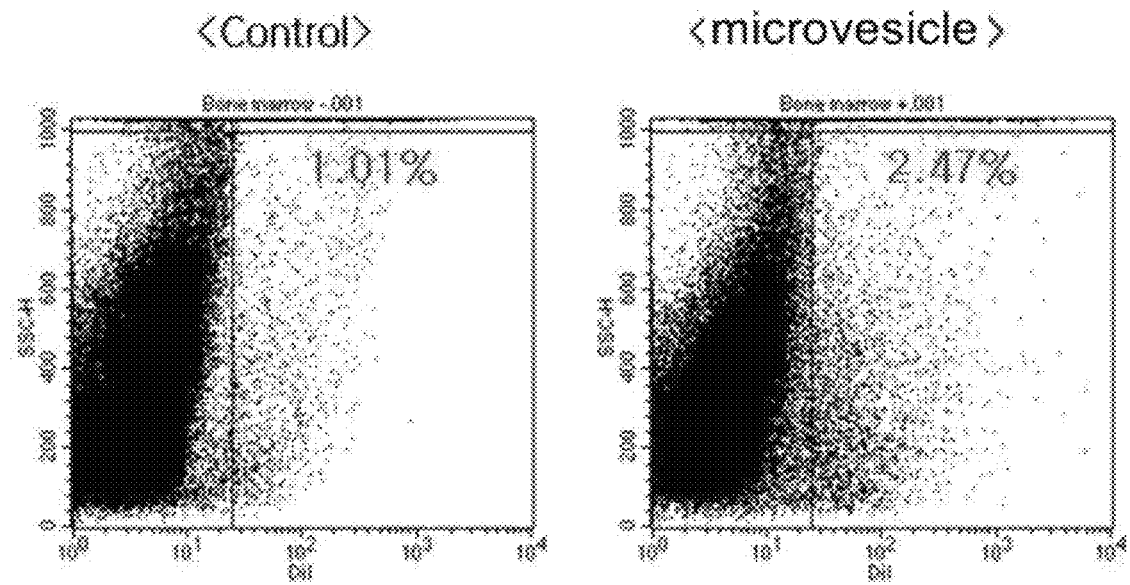
FIG. 40 is of images showing the bone marrow-derived microvesicles target the bone marrow.

FIG. 40 shows FACS analysis results. Mice which were not injected with microvesicles were used as a control. As shown in FIG. 40, the percentage of the cells with a DiI signal intensity of $2\times10^1$ or higher was 1.01% upon injection without the microvesicles, but increased about 2.5 times, that is, to 2.47%, upon injection with the microvesicles.

This result indicates that the microvesicles derived from the bone marrow targets the bone marrow.

To examine whether the microvesicles derived from the bone marrow can deliver doxorubicin to the bone marrow, doxorubicin-loaded microvesicles were generated from bone marrow cells according to the method of Example 9.

PBS, 80 μg of microvesicles, 24 μg of doxorubicin, or PBS containing 80 μg of microvesicles loaded with 24 μg of doxorubicin was injected at a dose of 100 μl into the tail vein of mice. Six hours after the injection, bone marrow cells were taken from each mouse and doxorubicin levels in the bone marrow were quantitatively analyzed. The doxorubicin levels were measured using fluorescence according to the method of Example 10. Bone marrow protein obtained from each mouse was normalized.

Figure 41:
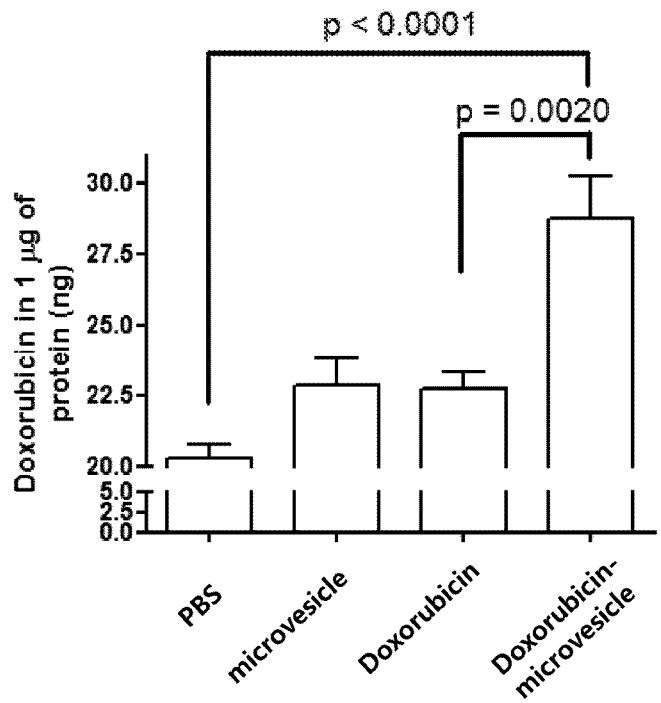
FIG. 41 is a graph showing the delivery of doxorubicin to the bone marrow by bone marrow-derived microvesicles.

FIG. 41 shows doxorubicin levels in 1 μg of protein obtained from the bone marrow of each group consisting of 3 mice. As seen in FIG. 41, the PBS control was observed to contain about 20 μg of doxorubicin per μg of protein whereas about 28 μg of doxorubicin was measured per μg of protein in the bone marrow of the mice administered with doxorubicin-microvesicles.

This result indicates that bone marrow-derived microvesicles can be used to deliver doxorubicin to the bone marrow. Doxorubicin was delivered in a significantly low amount to the bone marrow by itself, compared to the doxorubicin-microvesicles.

Example 27: Cell-Specific Delivery Using Transformed Cells

Doxorubicin-loaded microvesicles were prepared from ICAM-antisense-transformed HT1080 and ICAM-1 sense-transformed HT1080 cells according to the method of Example 9. The microvesicles were loaded with ICAM-1 when generated from ICAM-1 sense-transformed HT1080 cells, but not loaded with ICAM-1 when generated from ICAM-1 antisense-transformed HT1080 cells.

The monocyte U937 cells were seeded at a density of $1\times10^5$ cells/well into 24-well plates containing 500 μl per well, followed by incubation for 24 hours with the microvesicles generated from HT2 and HT3 at a concentration of 0, 0.2, 0.5, and 1 μg/ml. Thereafter, 50 μl of the cell solution was added to each well of 96-well plates prior to the addition of 50 μl of trypan blue. Viable cells are not stained with trypan blue because the dye is extracellularly secreted again.

In a hematocytometer was placed 10 µl of the mixture, after which cells devoid of trypan blue were counted.

Figure 42:
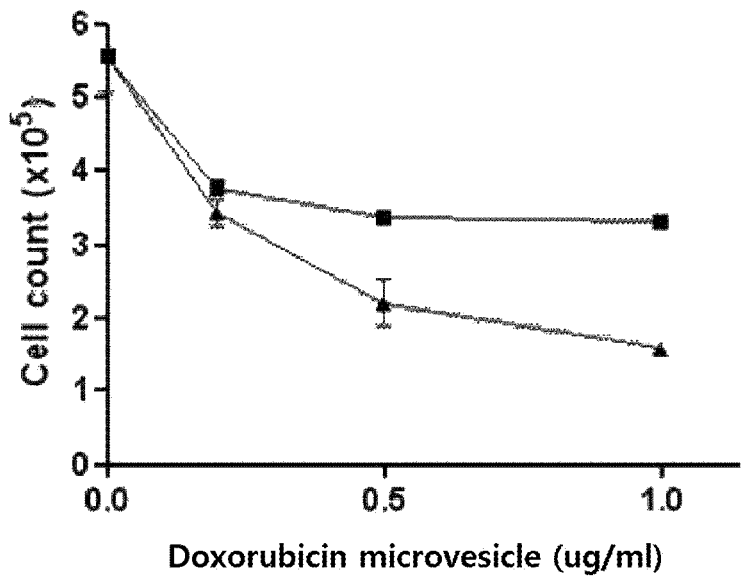
FIG. 42 is a graph showing the specific delivery of drug to monocytes by microvesicles constructed from nucleated cells transformed to express ICAM-1.

FIG. 42 is a graph showing viable cell counts measured in each test group. As can be seen in FIG. 42, the microvesicles derived from ICAM-1 sense-transformed HT1080 cells which expressed ICAM-1 capable of binding to LFA-1 on monocytes were found to induce the apoptosis of the monocyte U937 at higher efficiency than did those derived from ICAM-1 antisense-transformed HT1080 cells.

It is apparent from the data that the cell-specific delivery of substances can be achieved using microvesicles generated from cells which are transformed to express targeting substances.

Example 28: Isolation and Purification of Monocyte-Derived Shedding Microvesicles and Loading of Drug Thereto Ten mL of monocytes with a density of $1\times10^6$ cells/ml was incubated for 24 hours in the presence or absence of 10 µM cytochalasin D (Sigma, No. C8273). The conditioned media were centrifuged at 500× g for 10 min, after which the supernatant thus obtained were further subjected twice to centrifugation at 800× g for 10 min. Again, the resulting supernatant was ultracentrifuged at 100,000× g for 2 hours. The microvesicle pellets thus obtained were suspended in PBS.

FIG. 43 is a TEM image of the shedding microvesicles derived from cytochalasin D-treated cells.

As shown in FIG. 43, the shedding microvesicles ranged in size from about 50 to 100 nm.

Shedding microvesicles derived from cells treated with or without cytochalasin D-treated cells were incubated at 4° C. for 12 hours with 400 µg/ml doxorubicin. After incubation for 12 hours, the culture media were subjected to ultracentrifugation at 100,000× g for 2 hours. The pellets thus obtained were suspended in PBS to give doxorubicin-loaded shedding microvesicles.

Example 29: Isolation and Purification of Nanoparticle-Loaded Shedding Microvesicles The human uterine cervical cancer cell line HeLa (ATCC No. CCL-2) was seeded at a density of $1\times10^7$ cells into 150 mm plates, followed by incubation to 80% confluence. Carboxyl (—COOH)-coated Qdot 705 (Invitrogen, No. Q21361MP) was added at a concentration of 5 nM to 20 mL of a serum-free medium in which the cancer cells were then cultured for 24 hours. In this regard, the cells grown in a previous medium were washed well with PBS and then transferred to the Qdot-containing medium. After incubation for 24 hours, the conditioned media were harvested and centrifuged at 800× g for 10 min to remove cell debris, followed by centrifugation at 3000× g for 10 min. In this context, the centrifugation at 3000× g was performed in association with a centrifugation filter with a cutoff of 10 kDa so that 20 mL of the supernatant free of cell debris was concentrated to 3 mL. In a 5 mL ultracentrifugation tube were placed 1 mL of 50% OptiPrep, 1 mL of 5% OptiPrep and 3 mL of the concentrated conditioned medium in this order. Ultracentrifugation at 100,000× g for 2 hours formed a layer of Qdot-loaded shedding microvesicles between 50% OptiPrep and 5% OptiPrep.

Figure 44:
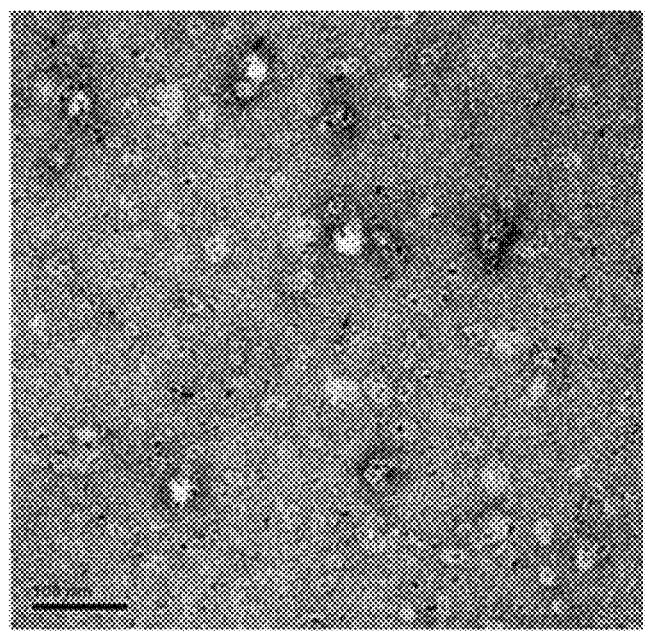
FIG. 44 is a TEM image showing shedding microvesicles loaded with the nanoparticles Q-dot.

FIG. 44 is a TEM image of the Qdot-loaded shedding microvesicles. Qdot appeared as black dots on the TEM image due to its high electron density. As shown in FIG. 44, Qdot particles were observed to exist at the same positions where most of the microvesicles were detected, demonstrating that nanoparticles such as quantum dots can be loaded to the shedding microvesicles.

Example 30: Cell-Specific Delivery of Drug by Monocyte-Derived, Doxorubicin-Loaded Shedding Microvesicles In 0.1% gelatin-coated 24-well plates was placed cover glass on which HUVEC cells were then seeded at a density of $3\times10^4$ cells/glass, followed by incubation for 12 hours. Subsequently, the cells were further incubated for 16 hours in the presence of 10 ng/ml TNF-α. They were washed with PBS, suspended in 500 µl of a medium and incubated for 20 min with 5 µg/ml of the monocyte-derived, doxorubicin-loaded shedding microvesicles generated according to the method of Example 27. Again, the cells were washed with PBS, suspended in 500 µl of a serum-free medium, and incubated for 30 min in the presence of 5 µM cell tracker. Subsequently, the cells were washed with PBS and incubated for 30 min in 500 µl of a medium supplemented with serum. The cover glass was fixed at room temperature for 10 min in 500 µl of 4% paraformaldehyde and covered with a slide glass before observation under a fluorescence microscope.

Figure 45:
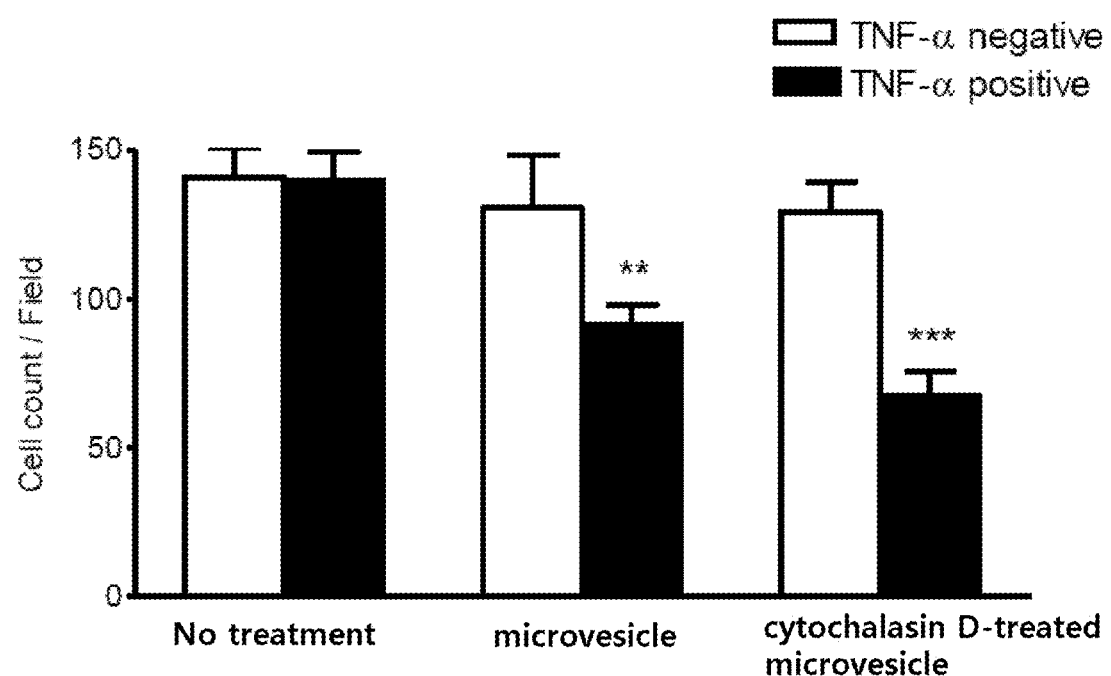
FIG. 45 is a graph showing the cell death of specific cells as a result of the delivery of doxorubicin by monocyte-derived shedding microvesicles.

FIG. 45 is a graph showing counts of viable cells after the drug delivery using the microvesicles. As can be seen from the data of FIG. 45, both of the doxorubicin-loaded shedding microvesicles, whether treated with or without cytochalasin D, induced the cells to undergo cell death.

From the higher apoptosis effect on TNF-α-treated HUVEC cells, it can be also inferred that the doxorubicin-loaded shedding microvesicles selectively induce apoptosis in cancer cells compared to normal cells.

Although the preferred embodiment(s) of the present invention have (has) been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described hitherto, the nucleated mammalian cell-derived microvesicles containing a therapeutic and/or diagnostic substance can deliver the substance to target cells or tissues selectively and effectively, whereby the possible adverse effect which might occur upon the delivery of the therapeutic substance to non-target can be eliminated, reducing the agony and inconvenience of cancer patients during treatment. In addition, the delivery of a diagnostic substance only to target cells or tissues makes it easy to accurately detect cells or tissues associated with diseases.

The invention claimed is:

1. A method of preparing a composition comprising sub-cell sized, nucleated mammalian cell-derived microvesicles for delivering a drug or a diagnostic substance to a target cell or tissue, comprising:
preparing a suspension of nucleated mammalian cells, and
conducting a serial extrusion with the nucleated mammalian cells by sequentially passing the cells through filters with diminishing micro-size pores to produce sub-cell sized microvesicles retaining the same membrane topology as that of the nucleated mammalian cells.

2. The method of claim 1, further comprising a step for loading a therapeutic or diagnostic substance in the microvesicles.

3. The method of claim 1, further comprising a step for mixing the nucleated mammalian cells with a medium containing a therapeutic or diagnostic substance.

4. The method of claim 2, wherein the step is collecting and incubating the microvesicles with a therapeutic or diagnostic substance.

5. The method of claim 2, wherein the step is electroporating a therapeutic or diagnostic substance into the microvesicles.

\* \* \* \* \*